United States Patent
Su et al.

(10) Patent No.: US 11,833,124 B2
(45) Date of Patent: *Dec. 5, 2023

(54) COMPOSITIONS AND METHODS FOR MODULATING HEXIM1 EXPRESSION

(71) Applicant: CASE WESTERN RESERVE UNIVERSITY, Cleveland, OH (US)

(72) Inventors: Bin Su, Cleveland, OH (US); Monica M. Montano, Cleveland, OH (US)

(73) Assignees: CASE WESTERN RESERVE UNIVERSITY, Cleveland, OH (US); CLEVELAND STATE UNIVERSITY, Cleveland, OH (US)

( * ) Notice: Subject to any disclaimer, the term of this patent is extended or adjusted under 35 U.S.C. 154(b) by 263 days.

This patent is subject to a terminal disclaimer.

(21) Appl. No.: 17/217,084

(22) Filed: Mar. 30, 2021

(65) Prior Publication Data

US 2021/0212969 A1    Jul. 15, 2021

Related U.S. Application Data

(63) Continuation of application No. 15/115,132, filed as application No. PCT/US2015/013844 on Jan. 30, 2015, now Pat. No. 10,959,966.

(60) Provisional application No. 61/933,370, filed on Jan. 30, 2014.

(51) Int. Cl.
| | | |
|---|---|---|
| *A61K 31/18* | (2006.01) | |
| *A61K 31/16* | (2006.01) | |
| *A61K 45/06* | (2006.01) | |

(52) U.S. Cl.
CPC .............. *A61K 31/18* (2013.01); *A61K 31/16* (2013.01); *A61K 45/06* (2013.01)

(58) Field of Classification Search
CPC ...................................................... A61K 31/18
See application file for complete search history.

(56) References Cited

U.S. PATENT DOCUMENTS

| 10,959,966 B2 * | 3/2021 | Su .......................... A61K 31/16 |
| 2005/0187179 A1 | 8/2005 | Miele et al. |

FOREIGN PATENT DOCUMENTS

WO    2011/109217 A2    9/2011

OTHER PUBLICATIONS

Zhong et al., Bioorganic & Medicinal Chemistry Letters, 2014, 24:1410-1413.*
Ketchart et al., Oncogene, 2013, 32(33): 3829-3839.*
Zhong, et al.; "Lead optimization of HMBA to develop potent HEXIM1 inducers"; Bioorganic and Medicinal Letters, Jan. 17, 2014, vol. 24, pp. 1410-1413.
Contreras et al.; "HMBA Releases P-TEFb from HEXIM1 and 7SK snRNA via PI3k/Akt and Activates HIV Transcription"; PLOS Pathogens, 2007, vol. 3, pp. 1459-1469.
Applicant: Case Western Reserve University; "Compositions and Methods for Modulating HEXIM1 Expression"; PCT Application No. PCT/US2015/013844, filed Jan. 30, 2015; International Search Report and Written Opinion dated Apr. 9, 2015; 9 pgs.
Li, et al.; A bisamide and four diketopiperazines from a marine-derived *Streptomyces* sp., 2011, Journal of Asian Natural Products Research, vol. 13, No. 12, pp. 1146-1150. (Year: 2011).
Ketchart, et al.; "Inhibition of metastasis by HEXIM1 through effects on cell invasion and angiogensis"; Oncognete (2013) vol. 32, 3829-3839; Macmillan Publishers Limited; www.nature.com/onc.; Published online Sep. 10, 2012; 11 pgs.; doi. 10.1038/onc.2012.405.

* cited by examiner

*Primary Examiner* — Rei Tsang Shiao

(74) *Attorney, Agent, or Firm* — TAROLLI, SUNDHEIM, COVELL & TUMMINO, LLP

(57) ABSTRACT

A method of inducing HEXIM1 expression in cells of a subject includes administering to the cells a compound having the formula,

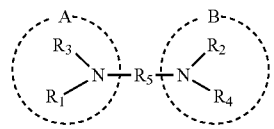

and pharmaceutically acceptable salts thereof.

21 Claims, 9 Drawing Sheets

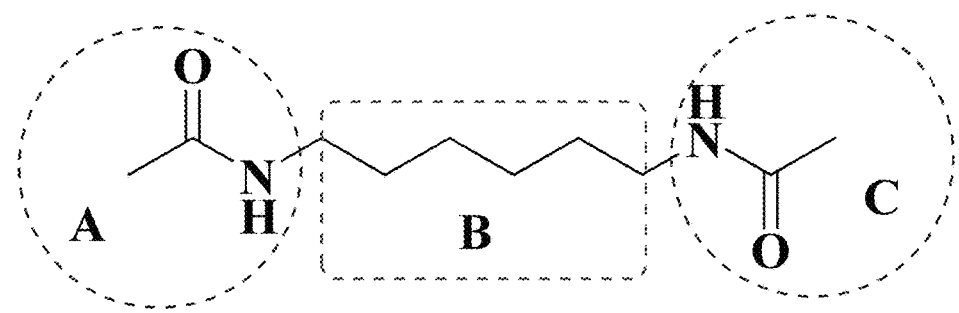
Fig. 1
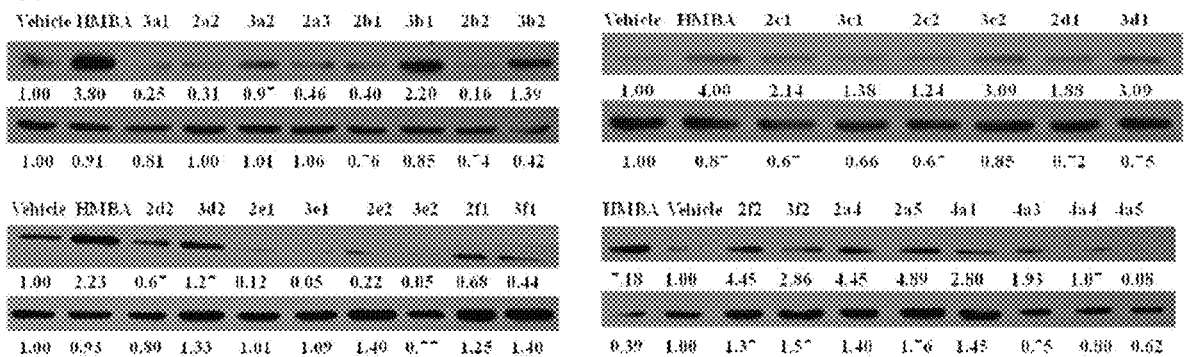
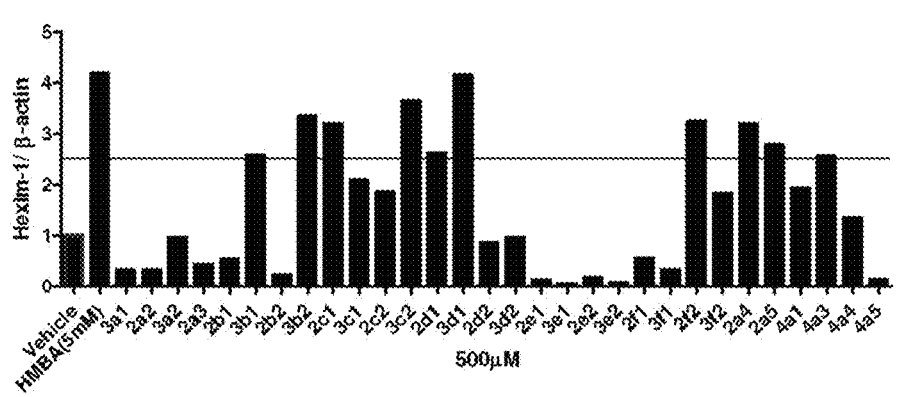
Figs. 2A-B

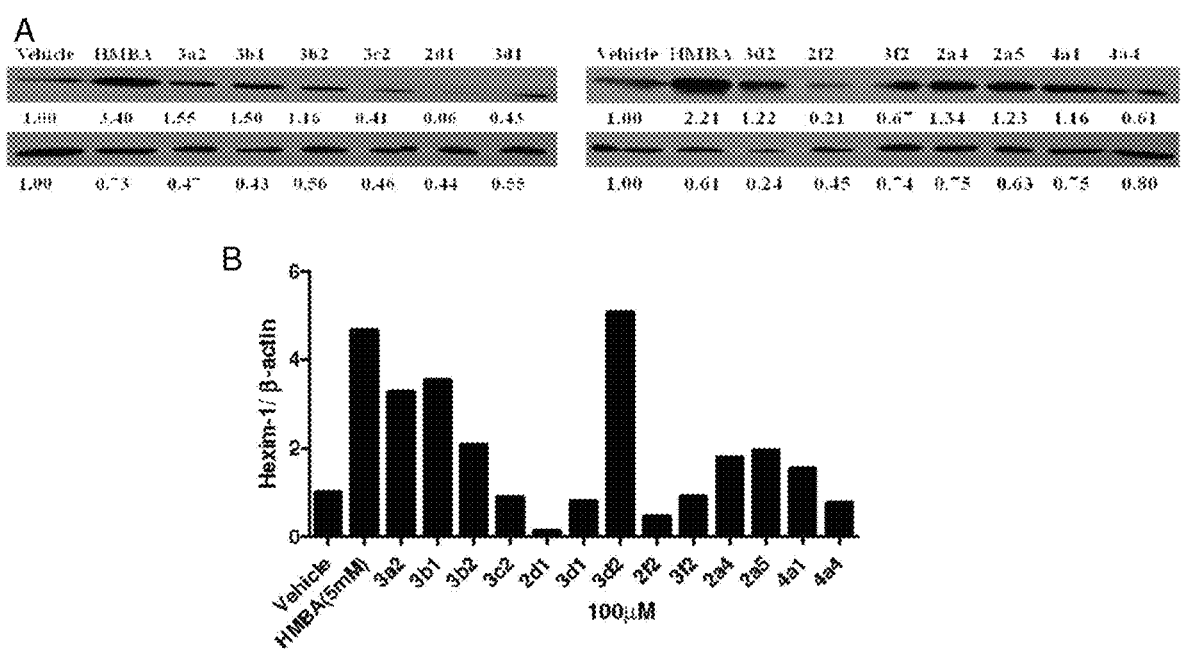
Figs. 3A-B
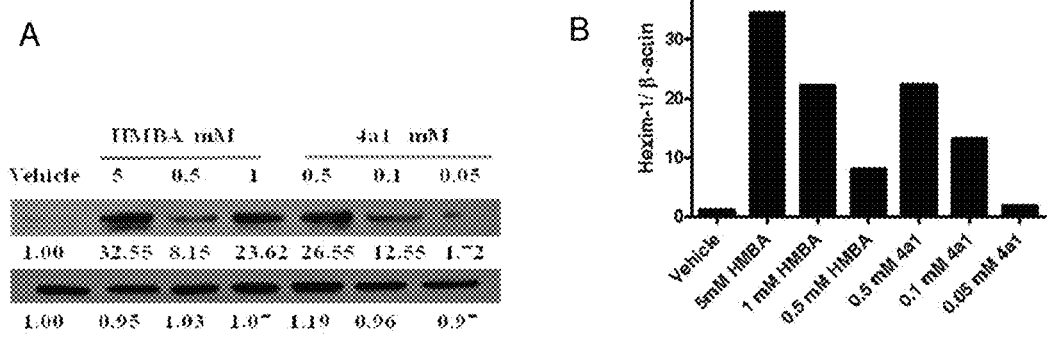
Figs. 4A-B

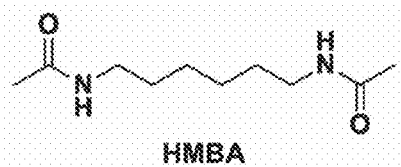
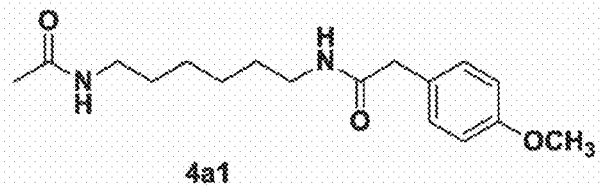
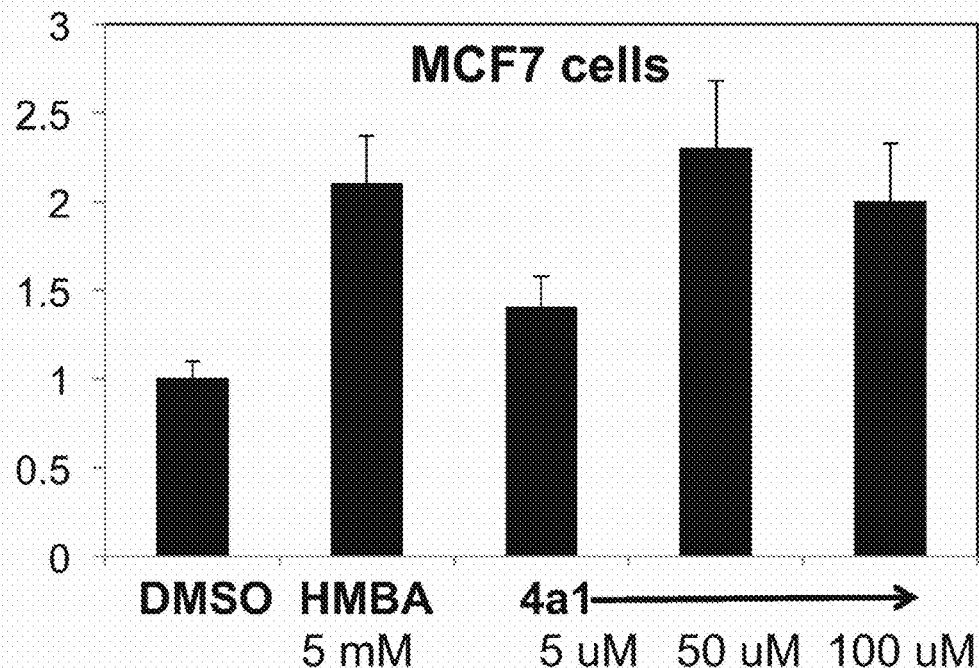
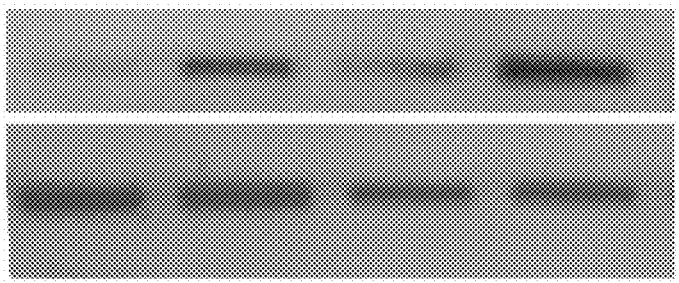
Figs. 5A-C

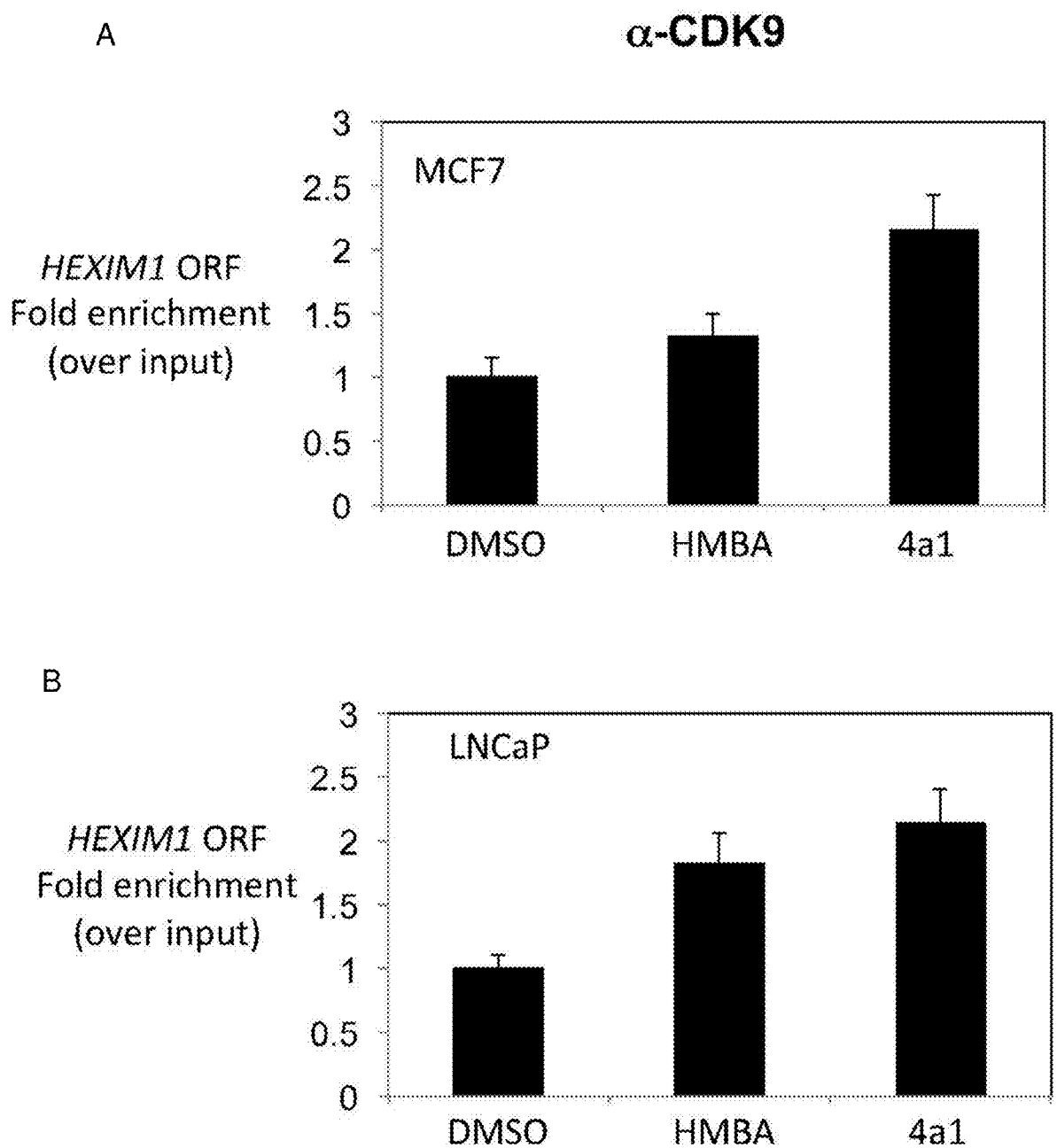
Figs. 6A-B

A. MCF7 cells
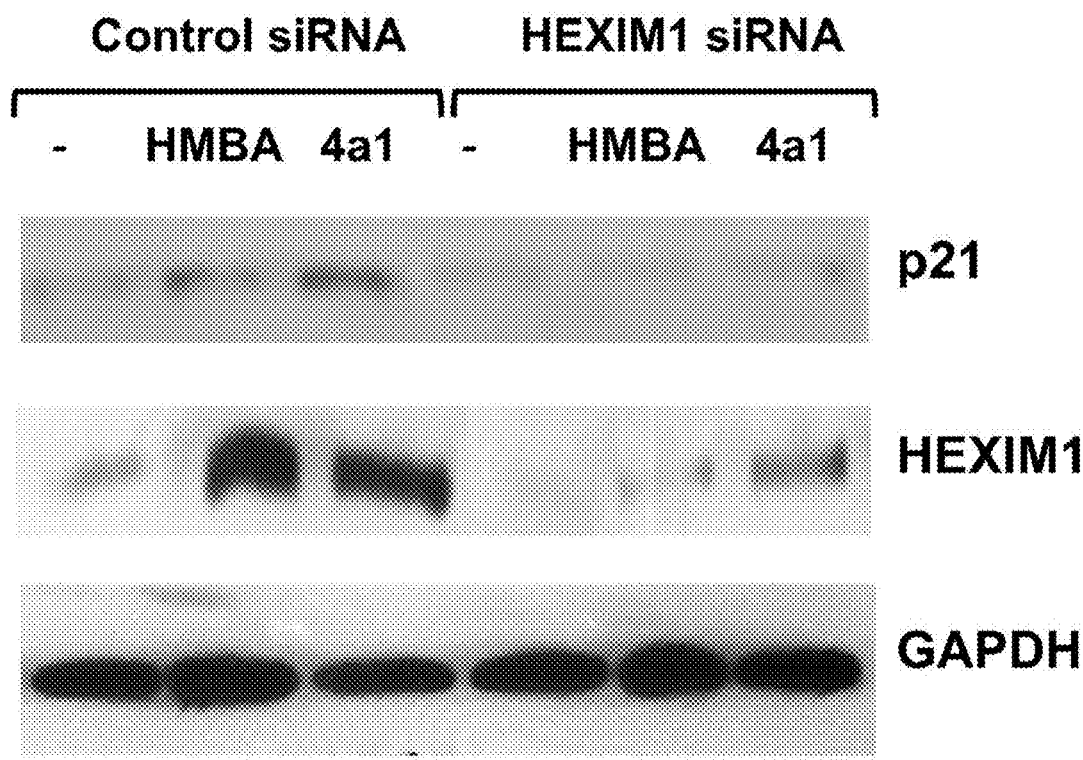
B. LNCaP cells
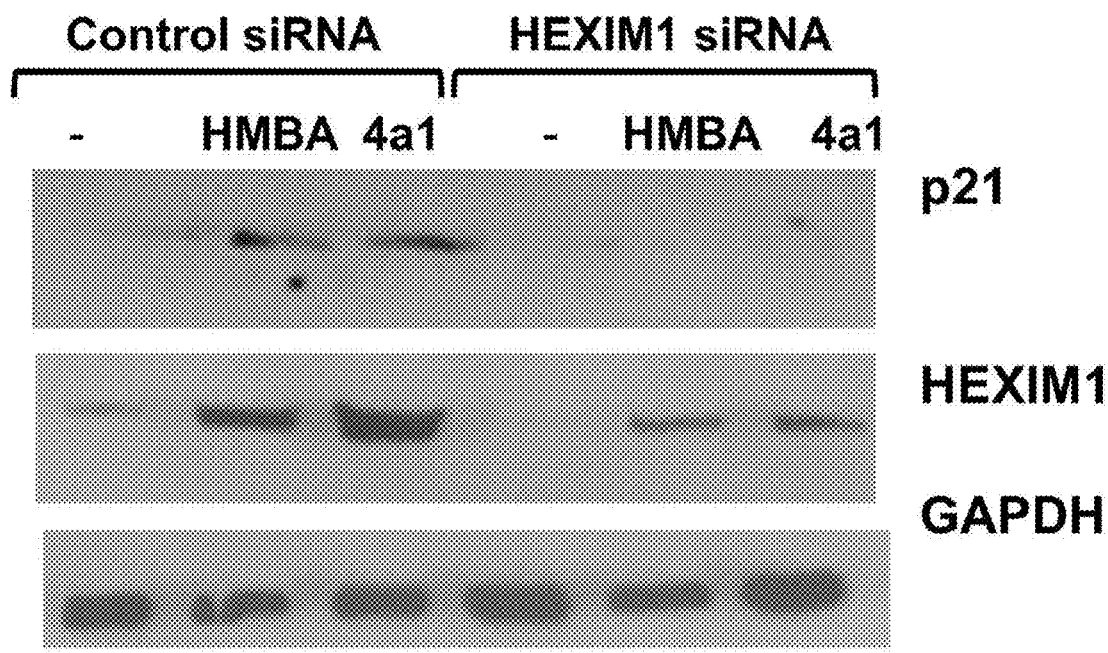
Figs. 7A-B

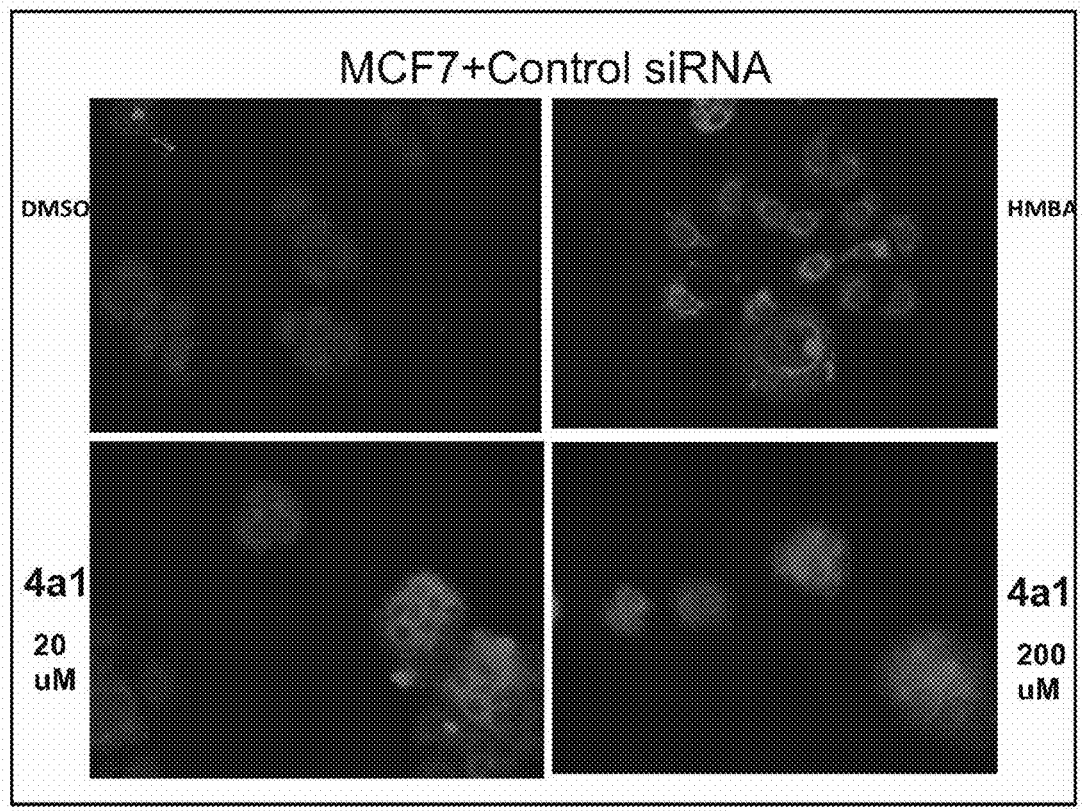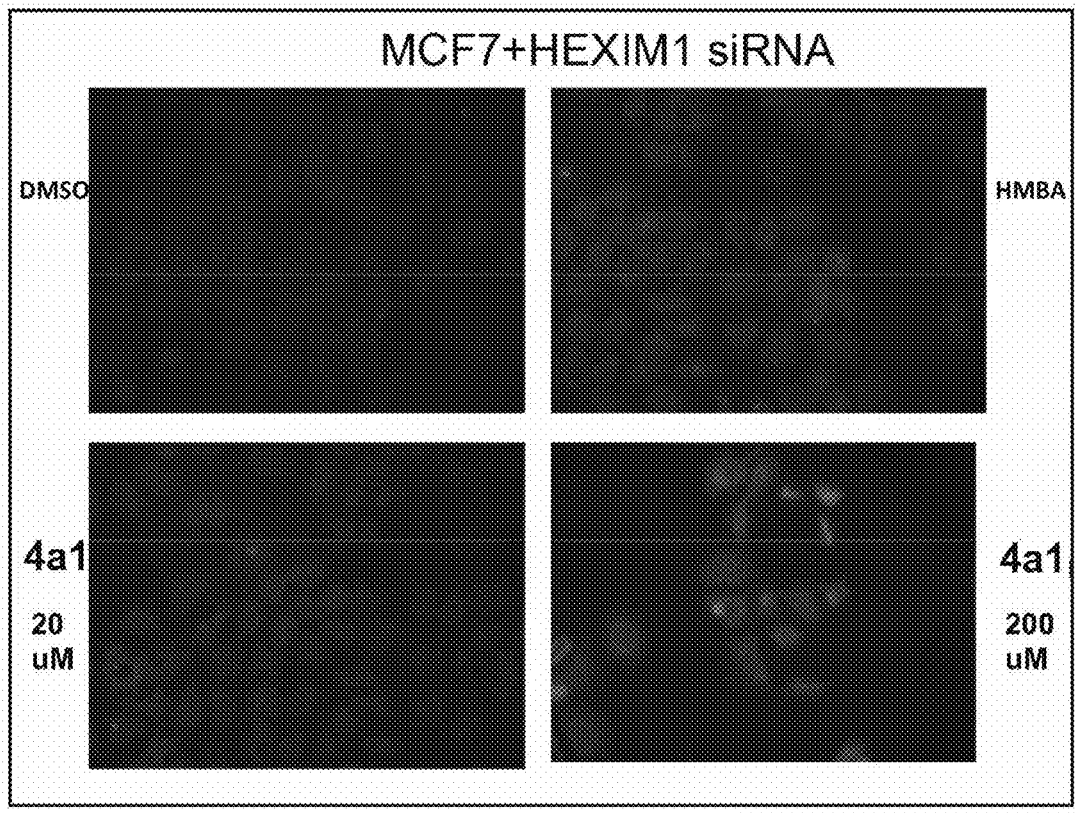
Fig. 8A

B. MDA-MB-231
control
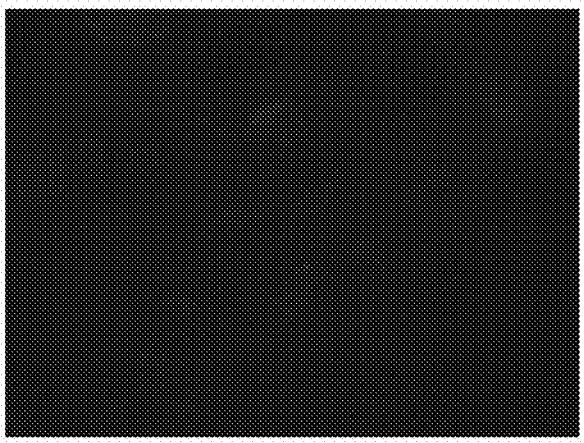
+flHEXIM1
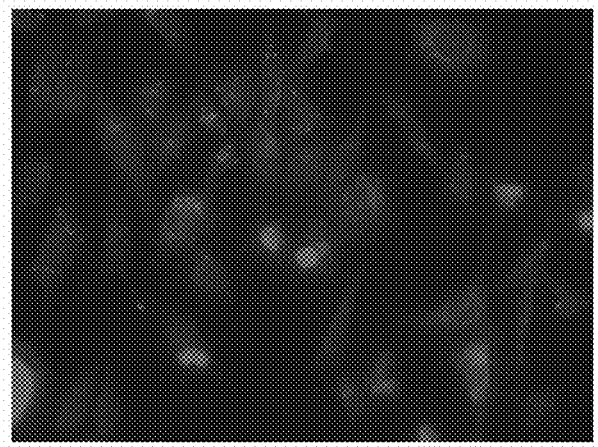
HMBA (5mM)
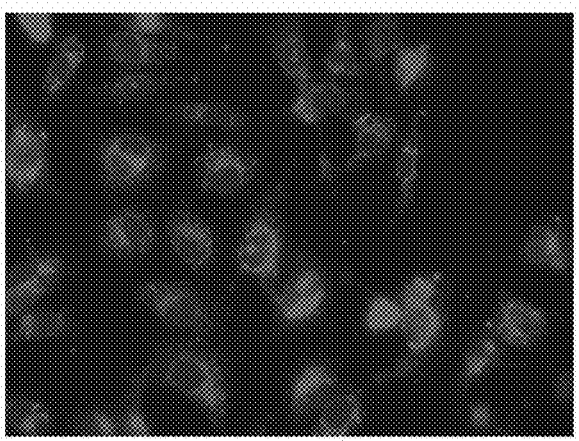
4a1 (20 uM)
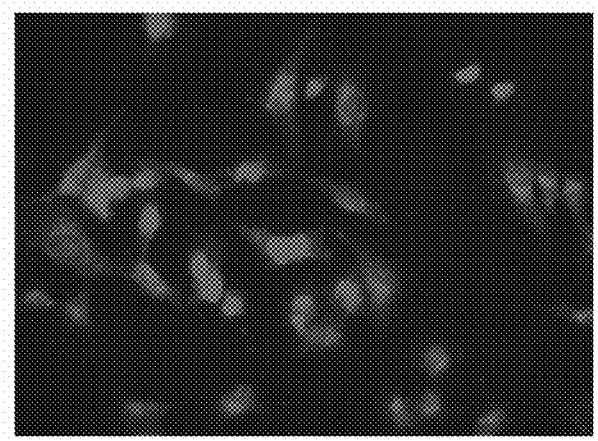
control  flHEXIM1
 HEXIM1
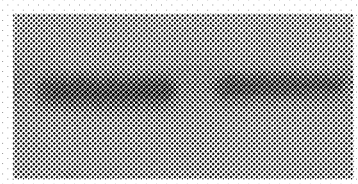 GAPDH
Fig. 8B

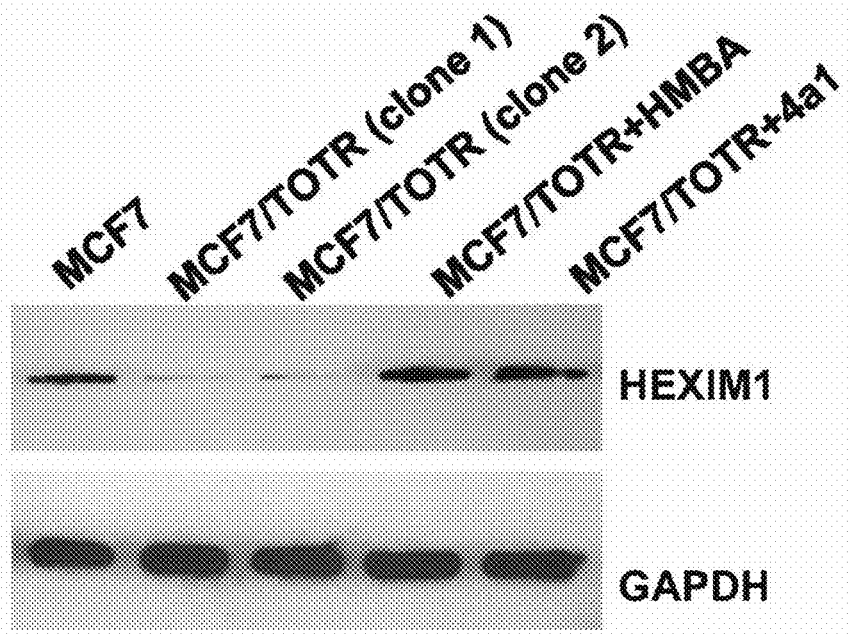
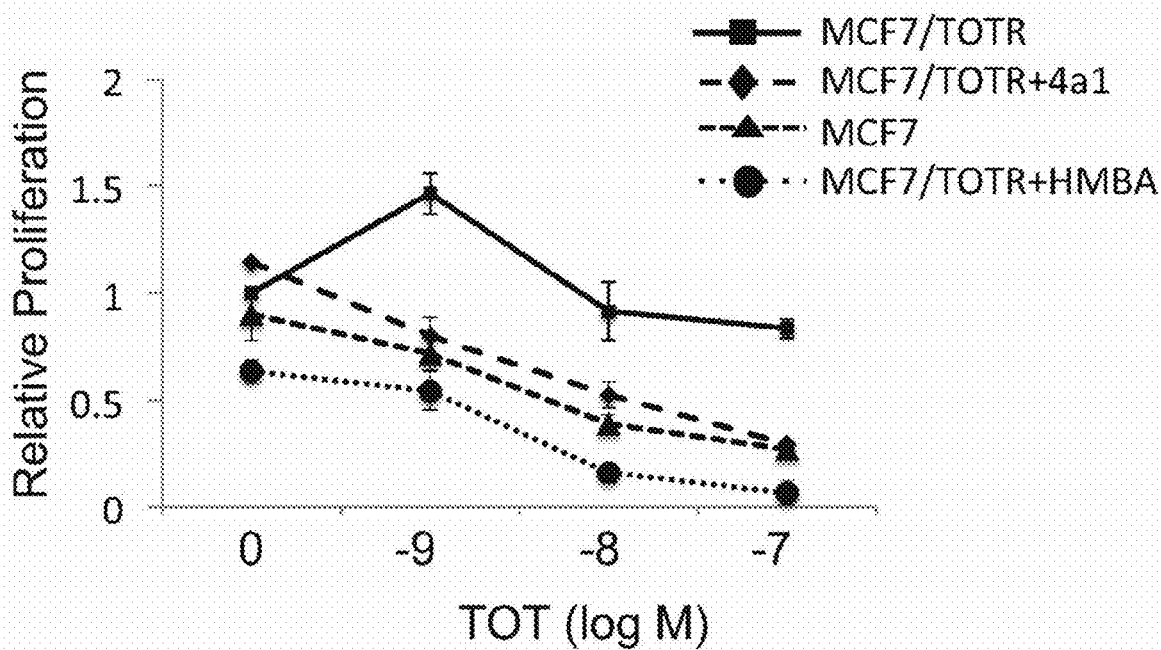
Figs. 9A-B

COMPOSITIONS AND METHODS FOR MODULATING HEXIM1 EXPRESSION

RELATED APPLICATION

This application claims priority from U.S. Provisional Application No. 61/933,370, filed Jan. 30, 2014, the subject matter of which is incorporated herein by reference in its entirety.

GOVERNMENT FUNDING

This invention was made with government support under Grant No. CA092440 awarded by The National Institutes of Health. The United States government has certain rights to the invention.

TECHNICAL FIELD

The present application relates to compositions for modulating HEXIM1 expression, and to hexamethylene bis-acetamide analogs for modulating HEXIM1 expression.

BACKGROUND

Hexamethylene bis-acetamide (HMBA) was investigated by the National Cancer Institute due to its potent anti-cancer and cell differentiation activities. The molecule failed at the Phase II clinical trial because of the dose-dependent toxicity. HMBA achieves its biological activity via Hexamethylene bis-acetamide inducible protein 1 (HEXIM1). HMBA significantly induces HEXIM1 expression in various cell lines at millimolar concentrations. However, for the agent to reach the active concentration in patients, it has to be administered via infusion of a high dosage, which can cause significant toxicity.

HEXIM1 binds to 7SK RNA, a highly abundant non-coding RNA. Together they act as potent inhibitors of positive transcription elongation b (P-TEFb) and lead to inhibition of transcription. The regulation of the relative ratio of inactive to active P-TEFb in cells by HEXIM1/7SK RNA plays a role in a wide range of cellular gene expression, such as estrogen and glucocorticoid receptor regulated genes. HEXIM1 also has an important role in heart development and remodeling. HEXIM1 expression is decreased in a model of pathological hypertrophy in the adult heart and decreased HEXIM1 expression augmented angiotensinogen induced pathological hypertrophy. Recent research suggests that HEXIM1 suppresses cancer metastasis and Human Immunodeficiency Virus (HIV) replication. HEXIM1 has also been reported to a play an inhibitory role in prostate tumorigenesis. Thus, drug candidates that can enhance the expression of HEXIM1 can have application in the treatment of cancer, heart disease, and acquired immunodeficiency syndrome (AIDS).

HMBA is the most potent and specific inducer for HEXIM1 thus far. However, this occurs only in in vitro cell cultures at concentrations ranging from one to five millimolars. It is difficult to reach high concentrations of HMBA in blood circulation due to its toxicity effects.

SUMMARY

Embodiments described herein relate to compositions and methods of modulating HEXIM1 expression in a cell of a subject. The compositions can include hexamethylene bis-acetamide analogs that when administered to cells of the subject can induce and/or promote HEXIM1 expression at a lower dosage and/or concentration compared to hexamethylene bis-acetamide. The cells can include, for example, cancer cells, smooth muscle cells, cardiomyocytes, and HIV infected cells. The compositions can be used in methods to treat cancer, heart disease, and HIV infection as well as promote cell differentiation including stem cell differentiation.

In some embodiments, the composition can include a compound having the formula:

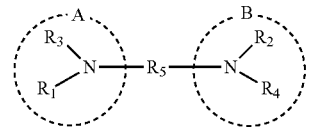

wherein $R_1$ and $R_2$ are the same or different and are one or more substituents selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido, imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl, arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide, phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, and phosphate esters;

$R_3$ and $R_4$ are the same or different and selected from the group consisting of hydrogen and substituted or unsubstituted $C_1$-$C_6$ alkyl;

$R_5$ is selected from the group consisting of a substituted or unsubstituted $C_2$-$C_6$ alkylene, $C_2$-$C_{24}$ alkenylene, $C_2$-$C_{24}$ alkynylene, $C_3$-$C_{20}$ arylene, heterocycloalkenylene containing from 5-6 ring atoms, heteroarylene or heterocyclylene containing from 5-14 ring atoms, $C_6$-$C_{24}$ alkarylene, and $C_6$-$C_{24}$ aralkylene;

at least one of A or B is an alkanamido group or alkanoylimino group, at least one of A or B is not an acetoamido group if $R_5$ is 1,6-hexylene; and pharmaceutically acceptable salts thereof; and a pharmaceutically acceptable carrier.

In some embodiments, the compound can induce HEXIM1 expression in cells administered the compound and exhibit negligible inhibition of histone diacetylene (HDAC) activity.

In other embodiments, $R_1$ and $R_2$ are the same or different and are each selected from the group consisting of substituted or unsubstituted alkanesulfonyl, alkanesulfinyl, alkanoyl, benzoyl, and aroyl, and wherein at least one of $R_1$ or $R_2$ is not an acetyl group if $R_3$ and $R_4$ are hydrogen and $R_5$ is hexylene; and pharmaceutically acceptable salts thereof.

In some embodiments, $R_5$ is selected from the group consisting of propylene, butylene, pentylene, hexylene, heptylene, octylene, nonylene, dodecylene, cyclohexylene, 1,4-cylohexylene-bis(methylene), 1,4-cylohexylene-bis(ethylene), 1,4-cylohexylene-bis(propylene), phenylene, 1,4-phenylene-bis(methylene), 1,4-phenylene-bis(ethylene), and 1,4-phenylene-bis(propylene); and pharmaceutically acceptable salts thereof.

In other embodiments, the compound can have the formula:

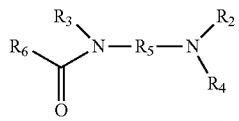

wherein $R_2$ is selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido, imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl, arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide, phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, and phosphate esters;

$R_3$ and $R_4$ are the same or different and selected from the group consisting of hydrogen and substituted or unsubstituted $C_1$-$C_6$ alkyl;

$R_5$ is selected from the group consisting of a substituted or unsubstituted $C_2$-$C_6$ alkylene, $C_2$-$C_{24}$ alkenylene, $C_2$-$C_{24}$ alkynylene, $C_3$-$C_{20}$ arylene, heterocycloalkenylene containing from 5-6 ring atoms, heteroarylene or heterocyclylene containing from 5-14 ring atoms, $C_6$-$C_{24}$ alkarylene, and $C_6$-$C_{24}$ aralkylene;

$R_6$ selected from the group consisting of substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), and arylcarbamoyl (—(CO)—NH-aryl);

$R_6$ is not a methyl group if $R_5$ is 1,6-hexylene, $R_2$ is an acetyl group, and $R_3$ and $R_4$ are hydrogen; and pharmaceutically acceptable salts thereof.

In still other embodiments, the compound can have the formula:

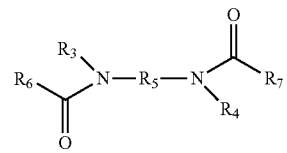

wherein $R_3$ and $R_4$ are the same or different and selected from the group consisting of hydrogen and substituted or unsubstituted $C_1$-$C_6$ alkyl;

$R_5$ is selected from the group consisting of a substituted or unsubstituted $C_2$-$C_6$ alkylene, $C_2$-$C_{24}$ alkenylene, $C_2$-$C_{24}$ alkynylene, $C_3$-$C_{20}$ arylene, heterocycloalkenylene containing from 5-6 ring atoms, heteroarylene or heterocyclylene containing from 5-14 ring atoms, $C_6$-$C_{24}$ alkarylene, and $C_6$-$C_{24}$ aralkylene;

$R_6$ and $R_7$ are the same or different and are selected from the group consisting of substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy (—O-acyl), $C_2$-$C_{24}$ alkoxycarbonyl (—(CO)—O— alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), and arylcarbamoyl (—(CO)—NH-aryl);

at least one of $R_6$ or $R_7$ is not a methyl group if $R_5$ is 1,6-hexylene and $R_3$ and $R_4$ are hydrogen; and pharmaceutically acceptable salts thereof.

In yet other embodiments, the compound can have the formula:

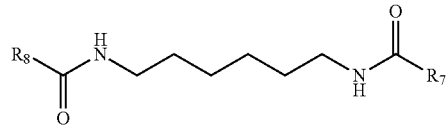

R$_7$ is selected from the group consisting of substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, and (—O-acyl);

R$_8$ is a linear or branched $C_1$-$C_{12}$ alkyl group; and pharmaceutically acceptable salts thereof.

In some embodiments, the compound can be administered to cells, such as cancer cells, progenitor cells, or stem cells, to induce differentiation of the cells. For example, the compound can be administered to a cancer cell or cancer stem cell at amount effective to induce differentiation of the cancer cell or cancer stem cell.

In other embodiments, the compound can be administered to metastatic cancer cells at an amount effective to inhibit at least one of cancer cell invasion, angiogenesis, and/or pre-metastatic niche formation.

In still other embodiments, myocardial cells of a subject can be administered the compound at an amount effective to promote at least one of vascularization, myocardial growth, or cardiac function in the subject.

In yet other embodiments, HIV-infected cells of a subject can be administered an amount of the compound effective to inhibit HIV replication.

BRIEF DESCRIPTION OF THE DRAWINGS

FIG. 1 illustrates an HMBA analog design.

FIGS. 2(A-B) illustrate Western blots and a graph showing the effect of HMBA analogs on HEXIM1 expression. LNCaP cells were treated with vehicle, HMBA (5 mM) and its analogs at 500 µM for 24 h. Level of HEXIM1 (upper panel) and β-actin (lower panel) was analyzed by Western blot of cell extracts with HEXIM1 antibody and β-actin antibody respectively. The bands of HEXIM1 were quantified using ImageJ (NIH) and normalized to β-actin. The results are the representative of three independent experiments.

FIGS. 3(A-B) illustrate Western blots and a graph showing lower concentration of HMBA analogs on HEXIM1 expression. LNCaP cells were treated with vehicle, HMBA (5 mM) and identified analogs at 100 µM for 24 h. Level of HEXIM1 (upper panel) and β-actin (lower panel) was analyzed by Western blot of cell extracts with HEXIM1 antibody and β-actin antibody respectively. The bands of HEXIM1 were quantified using ImageJ (NIH) and normalized to β-actin. The results are the representative of three independent experiments.

FIGS. 4(A-B) illustrate Western blots and a graph showing dose-dependent study of compound 4a1 and HMBA on HEXIM1 expression. Level of HEXIM1 (upper panel) and β-actin (lower panel) was analyzed by Western blot of cell extracts with HEXIM1 antibody and β-actin antibody respectively.

FIGS. 5(A-C) illustrate (A) the structure of HMBA analog, 4a1, (B) a graph showing HEXIM1 protein expression of breast cancer MCF7 cells treated with vehicle, HMBA, or 4a1 for 18 h, and (C) Western blot analyses of HEXIM1 targets relative to the loading control (GAPDH) of the treated cells.

FIGS. 6(A-B) illustrate graphs showing HEXIM1 graphs showing HMBA and 4a1 induced recruitment of CDK9 to HEXIM1 promoter in MCF7 and LNCaP cells treated with 5 mM HMBA or 50 µM 4a1 for 90 minutes.

FIGS. 7(A-B) illustrate Western blots showing (A) MCF7 (control siRNA or HEXIM1 siRNA) and (B) LNCaP (control shRNA or HEXIM1 shRNA) cells treated with vehicle (DMSO), 5 mM HMBA, or 50 µM 4a1 for 18 hours.

FIGS. 8(A-B) illustrate images showing (A) MCF7 cells transfected with control or HEXIM1 siRNA or (B) MDA-MB-231 transfected with control or HEXIM1 expression vector treated with vehicle (DMSO), HMBA, or 4a1 for 72 hours. Lower panels show Western blot analyses of HEXIM1 expression in MDA-MB-231 cells transfected with control or expression vector for Flag-tagged HEXIM1.

FIGS. 9(A-B) illustrate a Western blot and plots showing HEXIM1 expression in MCF7 and MCF7(TOTR) cells in the presence of vehicle (DMSO), 5 mM HMBA or 50 µM 4a1.

DETAILED DESCRIPTION

Figure 10:
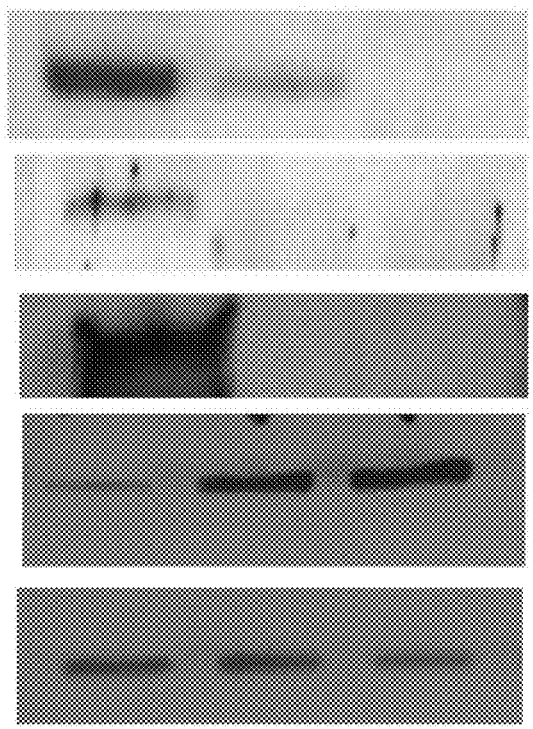
FIG. 10 illustrates a Western blot of MCF7 cells treated with vehicle, 5 mM HMBA, or 50 uM 4a1 for 18 h, and processes for analyses of HEXIM1 targets relative to GAPDH.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas sulfur bound to three or four different substituents, e.g., sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physico-chemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Fore example, the protecting group can be an amine protecting group or a hydroxyl protecting group. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo.

"Counterion" is used to represent a small, negatively charged species such as fluoride, chloride, bromide, iodide, hydroxide, acetate, and sulfate.

The term "sulfoxide" refers to a sulfur attached to 2 different carbon atoms and one oxygen and the S—O bond can be graphically represented with a double bond (S=O), a single bond without charges (S—O) or a single bond with charges [S(+)-O(−)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

The term "neoplasm" refers to any abnormal mass of cells or tissue as a result of neoplasia. The neoplasm may be benign, potentially malignant (precancerous), or malignant (cancerous). An adenoma is an example of a neoplasm.

The term "neoplastic cell" refers to a cell that shows aberrant cell growth, such as increased, uncontrolled cell growth. A neoplastic cell can be a hyperplastic cell, a cell from a cell line that shows a lack of contact inhibition when grown in vitro, a tumor cell, or a cancer cell that is capable of metastasis in vivo. Alternatively, a neoplastic cell can be termed a "cancer cell." Non-limiting examples of cancer cells can include lymphoma cells, melanoma cells, sarcoma cells, leukemia cells, retinoblastoma cells, hepatoma cells, myeloma cells, glioma cells, mesothelioma cells, carcinoma cells and adenocarcinoma cells.

The term "tumor" refers to an abnormal mass or population of cells that result from excessive cell division, whether malignant or benign, and all pre-cancerous and cancerous cells and tissues.

The terms "radiation therapy" or "radiotherapy" refers to the use of high-energy radiation from x-rays, gamma rays, neutrons, protons, and other sources to kill cancer cells and shrink tumors. Radiation may come from a machine outside the body (external-beam radiation therapy), or it may come from radioactive material placed in the body near cancer cells (internal radiation therapy). Systemic radiation therapy uses a radioactive substance, such as a radiolabeled monoclonal antibody, that travels in the blood to tissues throughout the body. The terms are intended to include without limitation ionizing radiation therapy, brachytherapy, sealed source radiation therapy, systemic radioisotope therapy, unsealed source radiotherapy, radionuclide therapy, external beam radiation therapy, radiation surgery, charged-particle radiotherapy, neutron radiotherapy, x-ray therapy, and cobalt therapy.

Term "ionizing radiation" means radiation comprising particles or photons that have sufficient energy or can produce sufficient energy via nuclear interactions to produce ionization (gain or loss of electrons). An exemplary ionizing radiation is an x-radiation or gamma-radiation.

The term "HIV" is used herein to refer to the human immunodeficiency virus. It is recognized that the HIV virus is an example of a hyper-mutable retrovirus, having diverged into two major subtypes (HIV-1 and HIV-2), each of which has many subtypes.

The terms "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). The term "expression levels" refers to a quantity reflected in or derivable from the gene or protein expression data, whether the data is directed to gene transcript accumulation or protein accumulation or protein synthesis rates, etc.

The terms "healthy" and "normal" are used interchangeably herein to refer to a subject or particular cell or tissue that is devoid (at least to the limit of detection) of a disease condition.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

Embodiments described herein relate to compounds, compositions, and methods for modulating HEXIM1 expression in a cell of a subject and to the use of such compounds, compositions, and methods for the treatment, inhibition, and management of diseases and disorders associated with hexamethylene bis-acetamide inducible protein 1 (HEXIM1) expression. HEXIM1 expression plays an important role in heart development and remodeling and suppresses cancer metastasis and human immunodeficiency virus (HIV) replication. Hexamethylene bis-acetamide (HMBA) is a potent and specific inducer of HEXIM1 expression at millimolar quantities in in vitro cell cultures. HMBA, however, is a water soluble molecule that has a short half-life and poor tissue distribution when administered in vivo to a subject being treated. At quantities effective to induce HEXIM1 expression in cells in vivo, HMBA can be potentially toxic.

It was found that symmetrical and unsymmetrical analogs or derivatives of HMBA can be synthesized that have lower water solubility compared to HMBA and induce and/or promote HEXIM1 expression in cells to which they are administered at potentially lower dosage, concentration, quantity, and/or amount compared HMBA. These HMBA analogs can be provided in compositions that when administered to a subject being treated can induce HEXIM1 expression in cells without thrombocytopenia.

The HMBA analogs or compounds described herein as well as compositions containing the compounds can provide a pharmacologic method for inducing, promoting, and/or elevating HEXIM1 expression levels in cells or tissue of a subject in need thereof. In some embodiments, the compounds can be administered to cells, such as cancer cells, progenitor cells, or stem cells, to induce differentiation of the cells. For example, the compounds can be administered to a cancer cell or cancer stem cell at amounts effective to induce differentiation or terminal differentiation of the cancer cell or cancer stem cell. In other embodiments, the compounds can be administered to cancer cells, such as metastatic cancer cells, at amounts effective to inhibit at least one of cancer cell invasion, angiogenesis, and/or pre-metastatic niche formation. In still other embodiments, myocardial cells of a subject can be administered the compounds at an amount effective to promote at least one of vascularization, myocardial growth, or cardiac function in the subject. In yet other embodiments, HIV-infected cells of a subject can be administered an amount of the compound effective to inhibit HIV replication.

HMBA analogs described herein can be synthesized based on the HMBA scaffold and then selected for their ability to induce HEXIM1 expression in an in vitro cell assay. For example, the synthesized HMBA analogs can be administered to cells, such as LNCaP prostate cancer cells, and the level of HEXIM1 in such cells can be measured using western blot analyses. The level of HEXIM1 expression of cells that are treated with a potential HMBA analog can be compared to control cells treated without the HMBA analog or with HMBA. Control cells (untreated or treated with HMBA) can be assigned a relative HEXIM1 expression value. Induction or promotion of HEXIM1 expression is achieved when the HEXIM1 expression relative to the control is increased at least about 1%, 5%, 10%, 15%, 20%, 30%, 50%, 75%, 100%, 200%, or more.

The solubility of the HMBA analogs and their potency can be compared to further select compounds that can induce and/or promote HEXIM1 expression in the cells. Selected HMBA analogs can then be assessed for activities advantageous for therapeutic use. For example, selected HMBA analogs can be assessed for regulation of HEXIM1 targets in cancer cells as well as their affect on cancer cell proliferation differentiation, metastasis, and apoptosis and compared with known cytotoxic agents of such cells as well as HMBA and other HMBA analogs.

In some embodiments, the HMBA analogs can include a compound having the formula:

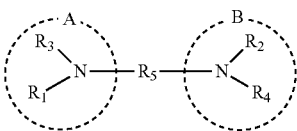

wherein $R_1$ and $R_2$ are the same or different and are one or more substituents selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido, imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl, arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide, phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)O]$_m$), phosphates, and phosphate esters;

$R_3$ and $R_4$ are the same or different and selected from the group consisting of hydrogen and substituted or unsubstituted $C_1$-$C_6$ alkyl;

$R_5$ is selected from the group consisting of a substituted or unsubstituted $C_2$-$C_6$ alkylene, $C_2$-$C_{24}$ alkenylene, $C_2$-$C_{24}$ alkynylene, $C_3$-$C_{20}$ arylene, heterocycloalkenylene containing from 5-6 ring atoms, heteroarylene or heterocyclylene containing from 5-14 ring atoms, $C_6$-$C_{24}$ alkarylene, and $C_6$-$C_{24}$ aralkylene;

at least one of A or B is an alkanamido group or alkanoylimino group, at least one of A or B is not an acetoamido group if $R_5$ is 1,6-hexylene; and pharmaceutically acceptable salts thereof; and a pharmaceutically acceptable carrier.

In other embodiments, $R_1$ and $R_2$ can be the same or different and can each be selected from the group consisting of substituted or unsubstituted alkanesulfonyl, alkanesulfinyl, alkanoyl, benzoyl, and aroyl, and wherein at least one of $R_1$ or $R_2$ is not an acetyl group if $R_3$ and $R_4$ are hydrogen and $R_5$ is hexylene; and pharmaceutically acceptable salts thereof.

In some embodiments, $R_5$ can be selected from the group consisting of propylene, butylene, pentylene, hexylene, heptylene, octylene, nonylene, dodecylene, cyclohexylene, 1,4-cylohexylene-bis(methylene), 1,4-cylohexylene-bis(ethylene), 1,4-cylohexylene-bis(propylene), phenylene, 1,4-phenylene-bis(methylene), 1,4-phenylene-bis(ethylene), and 1,4-phenylene-bis(propylene); and pharmaceutically acceptable salts thereof.

In some embodiments, the compound can induce HEXIM1 expression in cells administered the compound and exhibit negligible inhibition of histone diacetylene (HDAC) activity. HDAC activity can be measured, for example, using a colorimetric HDAC activity kit, such as is commercially available from BioVision.

In other embodiments, the compound can have the formula:

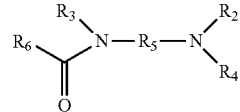

wherein $R_2$ is selected from the group consisting of substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkylcarbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—

(CO)-aryl), sulfanamido, imino, alkylimino, arylimino, nitro (—NO$_2$), nitroso (—NO), sulfo (—SO$_2$—OH), sulfonato (—SO$_2$—O$^-$), C$_1$-C$_{24}$ alkylsulfanyl, arylsulfanyl, C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), sulfonamide, phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, and phosphate esters;

R$_3$ and R$_4$ are the same or different and selected from the group consisting of hydrogen and substituted or unsubstituted C$_1$-C$_6$ alkyl;

R$_5$ is selected from the group consisting of propylene, butylene, pentylene, hexylene, heptylene, octylene, nonylene, dodecylene, cyclohexylene, 1,4-cylohexylene-bis(methylene), 1,4-cylohexylene-bis(ethylene), 1,4-cylohexylene-bis(propylene), phenylene, 1,4-phenylene-bis(methylene), 1,4-phenylene-bis(ethylene), and 1,4-phenylene-bis(propylene);

R$_6$ selected from the group consisting of substituted or unsubstituted C$_1$-C$_{24}$ alkyl, C$_2$-C$_{24}$ alkenyl, C$_2$-C$_{24}$ alkynyl, C$_3$-C$_{20}$ aryl, heterocycloalkenyl containing from 5-6 ring atoms, heteroaryl or heterocyclyl containing from 5-14 ring atoms, C$_6$-C$_{24}$ alkaryl, C$_6$-C$_{24}$ aralkyl, C$_1$-C$_{24}$ alkoxy, C$_2$-C$_{24}$ alkenyloxy, C$_2$-C$_{24}$ alkynyloxy, C$_5$-C$_{20}$ aryloxy, acyl, acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^-$), carbamoyl (—(CO)—NH$_2$), C$_1$-C$_{24}$ alkyl-carbamoyl (—(CO)—NH(C$_1$-C$_{24}$ alkyl)), and arylcarbamoyl (—(CO)—NH-aryl);

R$_6$ is not a methyl group if R$_5$ is 1,6-hexylene, R$_2$ is an acetyl group, and R$_3$ and R$_4$ are hydrogen; and pharmaceutically acceptable salts thereof.

In still other embodiments, the compound can have the formula:

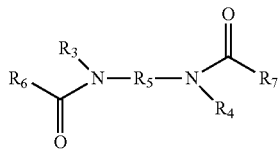

wherein R$_3$ and R$_4$ are the same or different and selected from the group consisting of hydrogen and substituted or unsubstituted C$_1$-C$_6$ alkyl;

R$_5$ is selected from the group consisting of propylene, butylene, pentylene, hexylene, heptylene, octylene, nonylene, dodecylene, cyclohexylene, 1,4-cylohexylene-bis(methylene), 1,4-cylohexylene-bis(ethylene), 1,4-cylohexylene-bis(propylene), phenylene, 1,4-phenylene-bis(methylene), 1,4-phenylene-bis(ethylene), and 1,4-phenylene-bis(propylene);

R$_6$ and R$_7$ are the same or different and are selected from the group consisting of substituted or unsubstituted C$_1$-C$_{24}$ alkyl, C$_2$-C$_{24}$ alkenyl, C$_2$-C$_{24}$ alkynyl, C$_3$-C$_{20}$ aryl, heterocycloalkenyl containing from 5-6 ring atoms, heteroaryl or heterocyclyl containing from 5-14 ring atoms, C$_6$-C$_{24}$ alkaryl, C$_6$-C$_{24}$ aralkyl, C$_1$-C$_{24}$ alkoxy, C$_2$-C$_{24}$ alkenyloxy, C$_2$-C$_{24}$ alkynyloxy, C$_5$-C$_{20}$ aryloxy, acyl, acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^-$), carbamoyl (—(CO)—NH$_2$), C$_1$-C$_{24}$ alkyl-carbamoyl (—(CO)—NH(C$_1$-C$_{24}$ alkyl)), and arylcarbamoyl (—(CO)—NH-aryl);

at least one of R$_6$ or R$_7$ is not a methyl group if R$_5$ is 1,6-hexylene and R$_3$ and R$_4$ are hydrogen; and pharmaceutically acceptable salts thereof.

In other embodiments, the compound can have the formula:

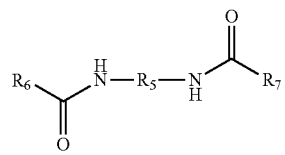

wherein R$_5$ is selected from the group consisting of propylene, butylene, pentylene, hexylene, heptylene, octylene, nonylene, dodecylene, cyclohexylene, 1,4-cylohexylene-bis(methylene), 1,4-cylohexylene-bis(ethylene), 1,4-cylohexylene-bis(propylene), phenylene, 1,4-phenylene-bis(methylene), 1,4-phenylene-bis(ethylene), and 1,4-phenylene-bis(propylene), R$_6$ and R$_7$ are the same or different and are selected from the group consisting of substituted or unsubstituted C$_1$-C$_{24}$ alkyl, C$_2$-C$_{24}$ alkenyl, C$_2$-C$_{24}$ alkynyl, C$_3$-C$_{20}$ aryl, heterocycloalkenyl containing from 5-6 ring atoms, heteroaryl or heterocyclyl containing from 5-14 ring atoms, C$_6$-C$_{24}$ alkaryl, C$_6$-C$_{24}$ aralkyl, C$_1$-C$_{24}$ alkoxy, C$_2$-C$_{24}$ alkenyloxy, C$_2$-C$_{24}$ alkynyloxy, C$_5$-C$_{20}$ aryloxy, acyl, acyloxy (—O-acyl), C$_2$-C$_{24}$ alkoxycarbonyl (—(CO)—O— alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^-$), carbamoyl (—(CO)—NH$_2$), C$_1$-C$_{24}$ alkyl-carbamoyl (—(CO)—NH(C$_1$-C$_{24}$ alkyl)), and arylcarbamoyl (—(CO)—NH-aryl); at least one of R$_6$ or R$_7$ is not a methyl group if R$_5$ is 1,6-hexylene; and pharmaceutically acceptable salts thereof.

In some embodiments, R$_6$ and R$_7$ are the same; while in other embodiments, R$_6$ and R$_7$ are different.

In yet other embodiments, the compound can have the formula:

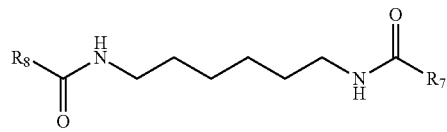

wherein R$_7$ is selected from the group consisting of substituted or unsubstituted C$_1$-C$_{24}$ alkyl, C$_2$-C$_{24}$ alkenyl, C$_2$-C$_{24}$ alkynyl, C$_3$-C$_{20}$ aryl, heterocycloalkenyl containing from 5-6 ring atoms, heteroaryl or heterocyclyl containing from 5-14 ring atoms, C$_6$-C$_{24}$ alkaryl, C$_6$-C$_{24}$ aralkyl, C$_1$-C$_{24}$ alkoxy, C$_2$-C$_{24}$ alkenyloxy, C$_2$-C$_{24}$ alkynyloxy, C$_5$-C$_{20}$ aryloxy, acyl, acyloxy, and (—O-acyl);

R$_8$ is a linear or branched C$_1$-C$_{12}$ alkyl group; and pharmaceutically acceptable salts thereof.

In some embodiment, $R_7$ is an unsubstituted or substituted alkyl, alkoxy, akylamino, aryl, alkylaryl, arylalkyl, alkoxy, aryloxy, alkylamino, arylamino, heteroaryl, or heterocyclyl, wherein the substituent can include one or more electron withdrawing or donating groups. For example, $R_7$ can be selected from the group consisting of a branched or linear alkyl,

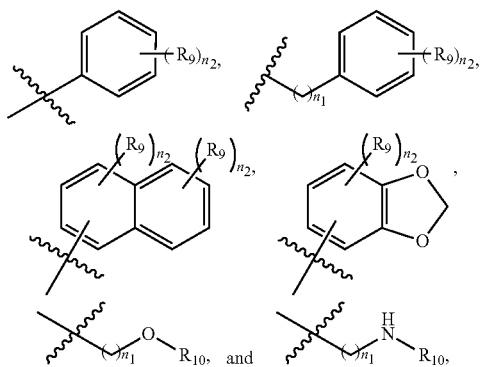

wherein $n_1$ is 0-7, $n_2$ is 0-3, $R_9$ is an electron donating or withdrawing group selected from the group consisting of OH, OMe, OAc, CN, $NO_2$, halo, —$(CH_2)n_3CH_3$ ($n_3$=0-7), phenyl, benzyl, $SO_2$, $SO_3$, alkylsulfonyl, amine, alkylamino, and carboxyl, $R_{10}$ is a linear or branched $C_1$-$C_{12}$ alkyl group or aryl group unsubstituted or substituted with an electron donating or withdrawing group selected from the group consisting of OH, OMe, OAc, CN, $NO_2$, halo, —$(CH_2)n_3CH_3$ ($n_3$=0-7), phenyl, benzyl, $SO_2$, $SO_3$, alkylsulfonyl, amine, alkylamino, and carboxyl; and pharmaceutically acceptable salts thereof.

In some embodiments, $R_8$ is a methyl, ethyl, propyl, or butyl group and $R_7$ is selected from the group consisting of

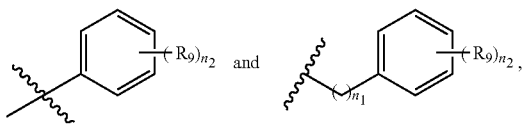

wherein $m_1$ is 9-7, $n_2$ is 0-3, $R_9$ is an electron donating or withdrawing group selected from the group consisting of OH, OMe, OAc, CN, $NO_2$, halo, —$(CH_2)n_3CH_3$ ($n_3$=0-7), phenyl, benzyl, $SO_2$, $SO_3$, alkylsulfonyl, amine, alkylamino, and carboxyl, and pharmaceutically acceptable salts thereof.

In still other embodiments, the compound can have the following formula:

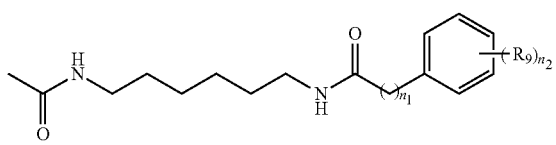

wherein $n_1$ is 1-7, $R_9$ is an electron donating or withdrawing group selected from the group consisting of OH, OMe, OAc, CN, $NO_2$, halo, —$(CH_2)n_3CH_3$ ($n_3$=0-7), phenyl, benzyl, $SO_2$, $SO_3$, alkylsulfonyl, amine, alkylamino, and carboxyl, and pharmaceutically acceptable salts thereof.

For example, the compound can have the following formula:

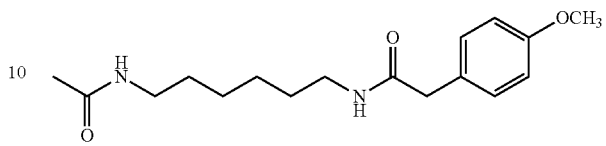

and pharmaceutically acceptable salts thereof.

In some embodiments, the HMBA analogs described herein can be provided in a pharmaceutical composition. The pharmaceutical composition can include a pharmaceutically or therapeutically effective amount of the HMBA analogs described above and a pharmaceutically acceptable diluent or carrier.

The pharmaceutical compositions can be provided in various forms, depending on the disorder to be treated and the age, condition, and body weight of the patient, as is well known in the art. Pharmaceutically acceptable compositions can be prepared by conventional means, and, if desired, the HMBA analogs described herein may be mixed with any conventional additive, such as an excipient, a binder, a disintegrating agent, a lubricant, a corrigent, a solubilizing agent, a suspension aid, an emulsifying agent, or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

The precise time of administration and/or amount of the HMBA analogs that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions can be prepared that are suitable for oral, nasal, topical (including buccal and sublingual), rectal, vaginal, aerosol, intravenous, systemic and/or parenteral administration. The pharmaceutical compositions may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Pharmaceutical compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes, and the like, each containing a predetermined amount of a therapeutic agent as an active ingredient. A compound may also be administered as a bolus, electuary or paste.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

The HMBA analogs described herein can be alternatively administered by aerosol. This is accomplished by preparing an aqueous aerosol, liposomal preparation, or solid particles containing the compound. A nonaqueous (e.g., fluorocarbon propellant) suspension could be used. Sonic nebulizers are preferred because they minimize exposing the agent to shear, which can result in degradation of the compound. Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids, such as glycine, buffers, salts, sugars, or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the therapeutic agent across the skin. The rate of such flux can be controlled by either providing a rate controlling membrane or dispersing the peptidomimetic in a polymer matrix or gel.

Pharmaceutical compositions suitable for parenteral or intravenous administration can include one or more the HMBA analogs described herein in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Pharmaceutical "slow release" capsules or "sustained release" compositions or preparations may be used and are generally applicable. Slow release formulations are generally designed to give a constant drug level over an extended period and may be used to deliver the agent. The slow release formulations are typically implanted in the vicinity of the target tissue, for example, the vicinity of a cancer or tumor or the vicinity of weakened, ischemic, and/or peri-infarct region of myocardial tissue.

Examples of sustained-release preparations include semipermeable matrices of solid hydrophobic polymers containing the HMBA analog, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid (e.g., poly(L-lactide-co-glycolide) (PLGA)) and copolymers, such as the LUPRON DEPOT (injectable microspheres composed of lactic acid-glycolic acid copolymer and leuprolide acetate); and poly-D-(–)-3-hydroxybutyric acid. Compositions including the HMBA analog and a biodegradable polymer, such as PLGA, can be administered to a subject to induce HEXIM1 expression in specific cells to which the composition is delivered without promoting thrombocytopenia in the subject.

While polymers, such as ethylene-vinyl acetate and lactic acid-glycolic acid enable release of molecules for over 100 days, certain hydrogels release proteins for shorter time periods. When encapsulated, the compound can remain in the body for a long time, and may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the compound. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap the HMBA analogs in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

When the HMBA analogs described herein are administered as pharmaceuticals to humans and animals, they can be given per se or as a pharmaceutical composition containing, for example, 0.1 to 99.5% (more preferably, 0.5 to 90%) of active ingredient in combination with a pharmaceutically acceptable carrier.

The HMBA analogs described herein or pharmaceutical compositions that include the HMBA analogs described herein can be administered to cells or tissue of a subject at amount effective to induce and/or promote HEXIM1 expression in the cells or tissue. The HMBA analogs can be administered ex vivo to cells isolated from the subject or in vivo to the subject.

In some embodiments, the HMBA analogs can be administered to cancer cells, such as breast cancer cells or prostate cancer cells, of a subject in need thereof to induce HEXIM1 expression in the cancer cells. Inducing HEXIM1 expression in the cancer cells can promote terminal differentiation of the cancer cells as well as inhibit at least one of cancer cell invasion, angiogenesis, and/or pre-metastatic niche formation.

Cancers that can be treated, prevented, or managed by methods employing the HMBA analogs and pharmaceutical compositions thereof can include but are not limited: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipidus; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America)

Accordingly, therapeutic methods employing the HMBA analogs described herein are useful in the treatment or prevention of a variety of cancers or other abnormal proliferative diseases, including (but not limited to) the following: carcinoma, including that of the bladder, breast, prostate, rectal, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoictic tumors of myeloid lineage, including acute and chronic myelogenous leukemias and promyclocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the skin, lung, colon, rectum, breast, prostate, bladder, kidney, pancreas, ovary, or uterus. In other specific embodiments, sarcoma, melanoma, or leukemia is treated or prevented.

In some embodiments, the cancer is malignant and underexpresses HEXIM1 compared to similar cancers. For example, the cancer can be metastatic breast cancer, prostate cancer, neuroblastoma, glioblastoma, leukemia, lymphoma, myeloma, melanoma, or colon cancer. In other embodiments, the disorder to be treated is a pre-cancerous condition associated with cells that underexpress HEXIM1.

In certain embodiments, the HMBA analogs described herein can be delivered to cancer cells by site-specific means. Cell-type-specific delivery can be provided by conjugating the HMBA analogs to a targeting molecule, for example, one that selectively binds to the affected cells. Methods for targeting include conjugates, such as those described in U.S. Pat. No. 5,391,723. Targeting vehicles, such as liposomes, can be used to deliver a compound, for example, by encapsulating the compound in a liposome containing a cell-specific targeting molecule. Methods for targeted delivery of HMBA analogs to particular cell types are well-known to those skilled in the art.

In other embodiments, the compound and a pharmaceutically acceptable carrier, such as biodegradable polymer, e.g., PLGA, can be administered to the subject induces HEXIM1 expression in the cancer cells without promoting thrombocytopenia in the subject.

In some embodiments, the HMBA analogs described herein can be used in combination and adjunctive therapies for inhibiting cancer cell metastasis, proliferation, and growth. The phrase "combination therapy" embraces the administration of the compositions described herein and an additional therapeutic agent as part of a specific treatment regimen intended to provide a beneficial effect from the co-action of these therapeutic agents. Administration of these HMBA analogs described herein in combination typically is carried out over a defined time period (usually minutes, hours, days or weeks depending upon the combination selected). The phrase "adjunctive therapy" encompasses treatment of a subject with HMBA analogs that reduce or avoid side effects associated with the combination therapy of this application.

A combination therapy is intended to embrace administration of the HMBA analogs described herein in a sequential manner, that is, wherein different therapeutic agents are administered at a different time, as well as administration of the HMBA analogs described herein, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of therapeutic agents can be effected by an appropriate routes including, but not limited to, oral routes, intravenous routes, intramuscular routes, and direct absorption through mucous membrane tissues. The therapeutic agents can be administered by the same route or by different routes. The sequence in which the therapeutic agents are administered is not narrowly critical.

Combination therapy also can embrace the administration of the HMBA analogs in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at a suitable time so long as a beneficial effect from the co-action of the combination of the HMBA analogs and radiation treatment is achieved. For example, in appropriate cases, the beneficial effect is still achieved when the radiation treatment is temporally removed from the administration of the therapeutic agents, perhaps by days or even weeks.

In some embodiments, the HMBA analogs described herein can be administered in combination with an anti-proliferative agent or anti-cancer agent. The phrase "anti-proliferative agent" and "anti-cancer agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms, such as biological response modification. There are large numbers of anti-proliferative agents available in commercial use, in clinical evaluation and in pre-clinical development, which can be included in this application by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Examples of anti-proliferative or anti-cancer agents that can be administered in combination with the HMBA analogs described herein include but are not limited to: acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decarbazine, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflomithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin 2 (including recombinant interleukin 2, or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nitrosoureas, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride. Other anti-cancer drugs include, but are not limited to: 20-epi-1,25 dihydroxyvitamin D3,5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, anti-dorsalizing morphogenetic protein-1, antiandrogens, antiestrogens, antineoplaston, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3, CARN 700, cartilage derived inhibitor, carzelesin, casein kinase inhibitors (ICOS), castanospermine, cecropin B, cetrorelix, chloroquinoxaline sulfonamide, cicaprost, cis-porphyrin, cladribine, clomifene analogs, clotrimazole, collismycin A, collismycin B, combretastatin A4, combretastatin analog, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexamethasone, dexifosfamide, dexrazoxane, dexverapamil, diaziquone, didemnin B, didox, diethylnorspermine, dihydro-5-azacytidine, dihydrotaxol, dioxamycin, diphenyl spiromustine, docetaxel, docosanol, dolasetron, doxifluridine, droloxifene, dronabinol, duocarmycin SA, ebselen, ecomustine, edelfosine, edrecolomab, eflomithine, elemene, emitefur, epirubicin, epristeride, estramustine analog, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analog, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogs, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall sk, mopidamol, multiple drug resistance gene inhibitor, multiple tumor suppressor 1 based therapy, mustard anticancer agent, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, porfimer sodium, porfiromycin, prednisone, propyl bis-acridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, R11 retinamide, rogletimide, rohitukine, romurtide, roquinimex, rubiginone B1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofiran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, taxol, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thioguanine, thrombopoietin, thrombopoietin mimetic, thymalfasin, thymopoietin receptor agonist, thymotrinan, thyroid stimulating hormone, tin ethyl etiopurpurin, tirapazamine, titanocene bichloride, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, and zinostatin stimalamer. Preferred additional anti-cancer drugs are 5-fluorouracil and leucovorin.

In certain embodiments, the HMBA analogs can be administered with an anti-cancer agent that induces stress in the cancer cells. The stress applied to the cancer cell can include, for example, radiation therapy or ionizing radiation, thermal stress or thermal therapy, irreversible electroporation (IRE), and oxidative stress.

Radiation therapy may include both "sealed" and "unsealed" sources of therapeutic radiation including, but not limited to, ionizing radiation therapy, brachytherapy, sealed source radiation therapy, systemic radioisotope therapy, unsealed source radiotherapy, radionuclide therapy, external beam radiation therapy, radiation surgery, charged-particle radiotherapy, neutron radiotherapy, x-ray therapy, and cobalt therapy.

Thermal stress or therapy can include focused ultrasound (FUS or HIFU), radiofrequency, infrared sauna, microwave heating, induction heating, magnetic hyperthermia, infusion of warmed liquids, or direct application of heat. The thermal stress can include local hyperthermia and/or regional hyperthermia. The thermal stress or thermal therapy can also include exposure to sub-lethal heat. For example, a hyperthermia modality may heat a cancer cell or microorganism too much lower therapeutic temperatures (in general <45° C.) compared to other tissue ablation techniques. For instance, the elevation above a normal body temperature of 37° C. typically will fall within a range of 42° C. to 45° C.

Irreversible electroporation uses a series of microsecond electrical pulses instead of extreme heat, freezing, radiation or microwave energy—to permanently open cell membranes in cancerous tumors. Once the cell membrane pores are opened, the death of the targeted cancer cells is induced. Surrounding veins, nerves and ducts within the targeted area are largely unaffected by the process around them, providing a compelling tool for procedures in difficult-to-treat parts of the body.

The exposure to stress may also be imaged guided. For example, clinical HIFU procedures are typically image-guided to permit treatment planning and targeting before applying a therapeutic or ablative level of ultrasound energy. When MRI is used for guidance, the technique is sometimes called Magnetic Resonance-guided Focused Ultrasound, often shortened to MRgFU. When ultrasonography is used, the technique is sometimes called Ultrasound-guided Focused Ultrasound, often shortened to USgFUS.

A subject having cancer, tumor, or at least one cancer or tumor cell, may be identified using methods known in the art. For example, the anatomical position, gross size, and/or cellular composition of cancer cells or a tumor may be determined using contrast-enhanced MRI or CT. Additional methods for identifying cancer cells can include, but are not limited to, ultrasound, bone scan, surgical biopsy, and biological markers (e.g., serum protein levels and gene expression profiles). An imaging solution comprising a cell-sensitizing composition of the present invention may be used in combination with MRI or CT, for example, to identify cancer cells.

The location(s) where HMBA analogs administered to the subject may be determined based on the subject's individual need, such as the location of the cancer cells (e.g., the position of a tumor, the size of a tumor, and the location of a tumor on or near a particular organ). For example, the cell-sensitizing composition may be injected directly (i.e., intratumorally) into a tumor. Alternatively, the HMBA analogs may be injected intravenously into the subject. It will be appreciated that other routes of injection may be used including, for example, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal routes.

Cancer therapies and their dosages, routes of administration and recommended usage are known in the art and have been described in such literature as the Physician's Desk Reference (56th ed., 2002).

In one specific embodiment, patients with breast cancer can be administered an effective amount of a compound described herein. In another embodiment, the HMBA analogs described herein can be administered in combination with an effective amount of one or more other agents useful for breast cancer therapy including but not limited to: tamoxifen, doxorubicin, epirubicin, the combination of doxorubicin and cyclophosphamide (AC), the combination of cyclophosphamide, doxorubicin and 5-fluorouracil (CAF), the combination of cyclophosphamide, epirubicin and 5-fluorouracil (CEF), herceptin, tamoxifen, the combination of tamoxifen and cytotoxic chemotherapy, taxanes (such as docetaxel and paclitaxel). In a further embodiment, HMBA analogs described herein can be administered with taxanes plus standard doxorubicin and cyclophosphamide for adjuvant treatment of node-positive, localized breast cancer.

In another specific embodiment, patients with pre-cancerous fibroadenoma of the breast or fibrocystic disease can be administered the HMBA analogs described herein to treat the disorder and decrease the likelihood that it will progress to malignant breast cancer. Additionally, patients refractory to treatment, particularly hormonal therapy, more particularly tamoxifen therapy, can be administered HMBA analogs described herein to treat the cancer and/or render the patient non-refractory or responsive.

In another embodiment, patients with colon cancer can be administered an effective amount of one or more HMBA analogs described herein. In yet another embodiment, HMBA analogs can be administered in combination with an effective amount of one or more other agents useful for colon cancer therapy including but not limited to: the combination of 5-FU and leucovorin, the combination of 5-FU and levamisole, irinotecan (CPT-11) or the combination of irinotecan, 5-FU and leucovorin (IFL).

In other embodiments, patients with prostate cancer can be administered an effective amount of one or more HMBA analogs described herein. In another embodiment, the HMBA analogs can be administered in combination with an effective amount of one or more other agents useful for prostate cancer therapy including but not limited to: external-beam radiation therapy, interstitial implantation of radioisotopes (i.e., $I^{125}$, palladium, iridium), leuprolide or other LHRH agonists, non-steroidal antiandrogens (flutamide, nilutamide, bicalutamide), steroidal antiandrogens (cyproterone acetate), the combination of leuprolide and flutamide, estrogens such as DES, chlorotrianisene, ethinyl estradiol, conjugated estrogens U.S.P., DES-diphosphate, radioisotopes, such as strontium-89, the combination of external-beam radiation therapy and strontium-89, second-line hormonal therapies such as aminoglutethimide, hydrocortisone, flutamide withdrawal, progesterone, and ketoconazole, low-dose prednisone, or other chemotherapy regimens reported to produce subjective improvement in symptoms and reduction in PSA level including docetaxel, paclitaxel, estramustine/docetaxel, estramustine/etoposide, estramustine/vinblastine, and estramustine/paclitaxel.

In a specific embodiment, patients with pre-cancerous high-grade prostatic intraepithelial neoplasia (PIN) are administered the HMBA analogs to treat the disorder and decrease the likelihood that it will progress to malignant prostate cancer.

In specific embodiments, patients with melanoma are administered an effective amount of HMBA analogs described herein. In another embodiment, the HMBA analogs can be administered in combination with an effective amount of one or more other agents useful for melanoma cancer therapy including but not limited to: dacarbazine (DTIC), nitrosoureas such as carmustine (BCNU) and lomustine (CCNU), agents with modest single agent activity including vinca alkaloids, platinum compounds, and taxanes, the Dartmouth regimen (cisplatin, BCNU, and DTIC), interferon alpha (IFN-A), and interleukin-2 (IL-2). In a specific embodiment, an effective amount of one or more HMBA analogs can be administered in combination with isolated hyperthermic limb perfusion (ILP) with melphalan (L-PAM), with or without tumor necrosis factor-alpha (TNF-alpha) to patients with multiple brain metastases, bone metastases, and spinal cord compression to achieve symptom relief and some shrinkage of the tumor with radiation therapy.

In specific embodiments, patients with ovarian cancer are administered an effective amount of one or more of the HMBA analogs described herein. In another embodiment, the HMBA analogs described herein can be administered in combination with an effective amount of one or more other agents useful for ovarian cancer therapy including but not limited to: intraperitoneal radiation therapy, such as $P^{32}$ therapy, total abdominal and pelvic radiation therapy, cisplatin, the combination of paclitaxel (Taxol) or docetaxel (Taxotere) and cisplatin or carboplatin, the combination of cyclophosphamide and cisplatin, the combination of cyclophosphamide and carboplatin, the combination of 5-FU and leucovorin, etoposide, liposomal doxorubicin, gemcitabine or topotecan. It is contemplated that an effective amount of one or more HMBA analogs can be administered in combination with the administration Taxol for patients with platinum-refractory disease. Included is the treatment of patients with refractory ovarian cancer including administration of: ifosfamide in patients with disease that is platinum-refractory, as salvage chemotherapy after failure of cisplatin-based combination regimens, and tamoxifen in patients with detectable levels of cytoplasmic estrogen receptor on their tumors.

In specific embodiments, patients with small lung cell cancer are administered an effective amount of one or more the HMBA analogs. In another embodiment, the HMBA analogs can be administered in combination with an effective amount of one or more other agents useful for lung cancer therapy including but not limited to: thoracic radiation therapy, cisplatin, vincristine, doxorubicin, and etoposide, alone or in combination, the combination of cyclophosphamide, doxorubicin, vincristine/etoposide, and cisplatin (CAV/EP), local palliation with endobronchial laser therapy, endobronchial stents, and/or brachytherapy.

In other specific embodiments, patients with non-small lung cell cancer are administered an effective amount of one or more HMBA analogs in combination with an effective amount of one or more other agents useful for lung cancer therapy including but not limited to: palliative radiation therapy, the combination of cisplatin, vinblastine and mitomycin, the combination of cisplatin and vinorelbine, paclitaxel, docetaxel or gemcitabine, the combination of carboplatin and paclitaxel, interstitial radiation therapy for endobronchial lesions or stereotactic radiosurgery.

In other embodiments, the HMBA analogs or compositions including the HMBA analogs described herein can be administered to a subject to treat cardiomyopathies and vasculopathies. Cardiomyopathies treated by the HMBA analogs and methods described herein can include but are not limited to diseases affiliated with decreases in HEXIM1 expression, such as cardiac hypertrophy. The cardiomyopathy treated by the HMBA analogs and methods can also include cardiomyopathies associated with a pulmonary embolus, a venous thrombosis, a myocardial infarction, a transient ischemic attack, a peripheral vascular disorder, atherosclerosis, ischemic cardiac disease and/or other myocardial injury or vascular disease.

The vasculopathy treated by the HMBA analogs and methods can include but is not limited to aneurysmal disease including Marfan's-related syndromes, aortic aneurysmal dilatation, cerebral aneurysmal dilatations, inflammatory aneurysms, Loey-Dietz syndrome, TGF beta aortopathies, cerebral cavernosus malformations (CCM disease), and other diseases of this nature.

It has been shown that cardiac hypertrophy often occurs after myocardial infarction. Various types of heart disease are also associated with hypertrophic conditions, most notably hypertensive cardiomyopathy and hypertrophic cardiomyopathy (HC). Hypertensive cardiomyopathy often presents with left ventricular hypertrophy in association with features of dilated cardiomyopathy or restrictive cardiomyopathy with cardiac failure. HC, which is more prevalent, is characterized by a thickening of abnormal heart tissue which can result in shortness of breath, progressive heart failure, and sudden death.

It was found that HMBA analogs that induce HEXIM1 expression in cardiomyocytes of subjects having or at risk of hypertrophic cardiomyopathy can potentially inhibit cardiac hypertrophy in the subject and promote at least one of vascularization, myocardial growth, and/or cardiac function.

The HMBA analogs described herein can be administered systemically or locally to weakened myocardial tissue, ischemic myocardial tissue, and/or apoptotic myocardial tissue, such as the peri-infarct region of a heart following myocardial infarction.

In some embodiments, the amount, concentration, and volume of HMBA analog administered to a subject can be controlled and/or optimized to substantially improve the functional parameters of the heart or vascular tissue while mitigating adverse side effects.

In some embodiments, the amount of HMBA analog administered to a myocardial tissue, such as a weakened region, ischemic region, and/or peri-infarct region of the myocardial tissue of the large mammal can be an amount effective to improve at least one functional parameter of the myocardium, such as a decrease in left ventricular end systolic volume, increase in left ventricular ejection fraction, decrease in wall motion score index, decrease in left ventricular end diastolic length, decrease in left ventricular end systolic length, decrease in left ventricular end diastolic area (e.g., mitral valve level and papillary muscle insertion level), decrease in left ventricular end systolic area (e.g., mitral valve level and papillary muscle insertion level), decrease in left ventricular end diastolic volume measured using, for example, using echocardiography, decrease in posterior wall thickness and LV mass to body weight ratios, increase in ejection fraction (EF %), increase in fractional shortening (FS), decrease in ejection time (ET) and decrease in isovolumic relaxation times (IVRT) indicating improvements of systolic and diastolic function and chamber filling.

The amount of the HMBA analogs described herein administered to a myocardial tissue can also be an amount effective to delay the emergence of hypertrophic cardiomyopathy or reverse the pathological course of the disease; inhibit left ventricular hypertrophy; cardiac hypertrophy regression, normalize systolic and diastolic function in heart; and restore normal cross-bridge behavior at the myofilament level.

In other embodiments, the HMBA analogs described herein or compositions including the HMBA analogs can be administered to HIV infected cells to inhibit HIV replication. HEXIM1 can complex with 7SK RNA complex and bind CDK9/CyclinT (P-TEFb) as part of the 7SK snRNP. P-TEFb serves not only as a general transcription factor but also a specific cellular cofactor for the HIV-1 Tat protein. Preventing Pol II from stalling is essential for HIV-1 transcription, during which P-TEFb is recruited to the nascent mRNA by Tat through formation of a ternary complex containing P-TEFb, Tat, and the HIV-1 TAR RNA, a stem-loop structure formed by the 5' end of the nascent viral transcript. Once recruited, P-TEFb phosphorylates the CTD and stimulates transcriptional elongation to produce the full-length HIV-1 transcripts.

The HMBA analogs described herein can be administered to HIV infected cells at amounts effective to induce HEXIM1 expression in the cells. The HMBA analogs can be administered according to well-established methodologies (osmotic pump, intracoronary injection, infusion, etc.). In particular, applicable protocols for administration of the HMBA analogs can be readily derived from the extensive clinical trials of HMBA for the treatment of acute myelogenous leukemia. In one exemplary method, the HMBA analogs can be administered by intravenous infusion.

Optimum dosages, toxicity, and therapeutic efficacy of such compounds may vary depending on the relative potency of individual compounds and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the HIV infected cells to minimize potential damage to normal cells and, thereby, reduce side effects. In addition, combinations of compounds having synergistic effects described herein can be used to further reduce toxic side effects of one or more agents comprising a pharmaceutical composition of the invention.

The data obtained from, for example, cell culture assays and animal studies can be used to formulate a dosage range for use in humans. The dosage of such small molecule compounds lies preferably within a range of circulating concentrations that include the $ED_{50}$ with little or no toxicity. The dosage can vary within this range depending upon the dosage form employed and the route of administration. For any compounds used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of compounds is from about 1 ng/kg to 100 mg/kg for a typical subject.

Following successful treatment, it may be desirable to have the subject undergo maintenance therapy to prevent the recurrence of the condition or disease treated.

Although the forgoing invention has been described in some detail by way of illustration and example for clarity and understanding, it will be readily apparent to one ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

As can be appreciated from the disclosure above, the present invention has a wide variety of applications. The invention is further illustrated by the following examples, which are only illustrative and are not intended to limit the definition and scope of the invention in any way.

EXAMPLE

We designed and synthesized HMBA symmetrical and unsymmetrical analogs or derivatives. The structure of HMBA is represented as three different moieties, A, B and C, (FIG. 1), which was used as the basis for our combinatorial chemistry approach to generate the new analogs. HMBA is a water-soluble molecule, which contributes greatly to its short half-life and poor tissue distribution. In the compound design, we introduced functional groups that can increase the hydrophobicity of the molecule.

The synthesis of the symmetrical and unsymmetrical derivatives is described in Scheme 1 and 2, respectively. For the symmetrical analogs, moieties A and C were kept identical. Besides the acetyl group of HMBA, methanesulfonyl group, propionyl group or butyryl group were introduced. In addition, a bulky benzoyl group was introduced. The active proton in the amide moiety was replaced with methyl group to generate a series of analogs with lower solubility. For the moiety B, various linkers such as 1,3-propylene, 1,5-propylene 1,4-cyclohexylene, 1,4-phenylene-bis(methylene), 1,4-cyclohexylene-bis (methylene) were tested for optimization. For the unsymmetrical analogs, the A and B moieties were kept the same as HMBA while the C moiety was modified with aryl or alkyl amide. A total of 32 compounds were synthesized, and these compounds were examined for their potency to induce HEXIM1 in LNCaP prostate cancer cells. HMBA (5 mM) was used as a positive control.

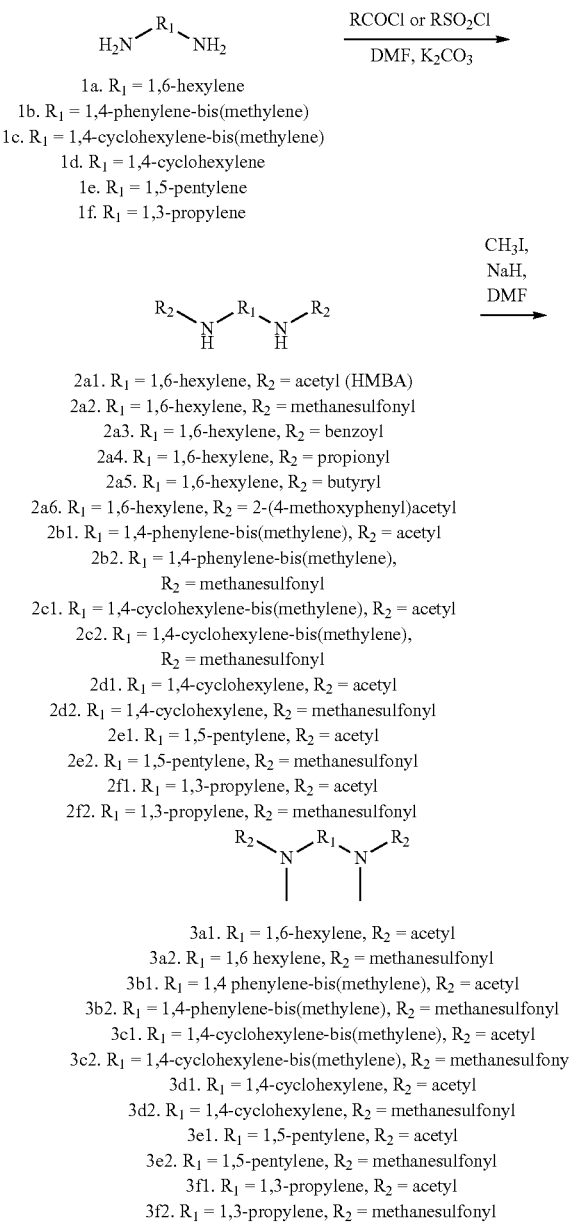

Scheme 2. Synthesis of unsymmetrical HMBA analogs

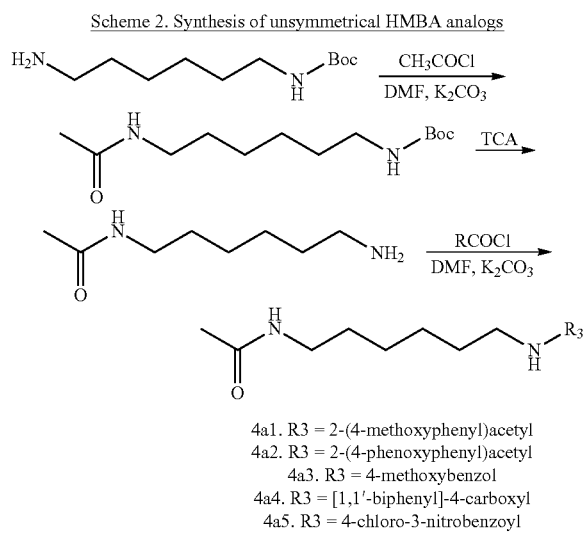

4a1. R3 = 2-(4-methoxyphenyl)acetyl
4a2. R3 = 2-(4-phenoxyphenyl)acetyl
4a3. R3 = 4-methoxybenzol
4a4. R3 = [1,1'-biphenyl]-4-carboxyl
4a5. R3 = 4-chloro-3-nitrobenzoyl The biological activities of HMBA analogs were determined by assessing HEXIM1 expression using western blot analyses. The analogs were screened at 500 µM, a concentration that was 10 times lower than the concentration of HMBA used. Cell morphology was examined after the treatment to exclude compounds that caused cell toxicity. An increment of 2.5 fold in HEXIM1 expression compared to the control was set as a cutoff to select candidates for further analyses. In addition, solubility and structural characteristics were considered when selecting the candidates. Among the derivatives, 3b1, 3b2, 3c2, 2d1, 3d1, 2f2, 2a4 and 2a5 induced HEXIM1 expression above 2.5 fold compared to the vehicle treatment (FIG. 2). Compounds 2c1 and 4a3 also reached this cutoff. However, cell morphology slightly changed after the treatment with these two compounds, which excluded them from further investigation. Compounds 3a2, 3d2, 3f2 did not reach the cutoff for HEXIM1. The reason could be that precipitation of these compounds during the treatment hindered entry to cells. Therefore, these three compounds were screened at lower concentrations. Compounds 4a1 and 4a4 have unsymmetrical novel structure, and are selected as candidates for further optimization. These two compounds were included for further analysis even if they did not reach the cutoff. Structurally, the aromatic and cyclohexylene moiety in compounds 3b1, 3b2, 2c1, 3c2, 2d1, and 3d1 resulted in enhanced activity. Compounds 2a4 and 2a5 with terminal propionyl and butyryl moieties exhibited better potency as well, suggesting that the bigger alkyl group at the terminal moiety allowed for enhanced activity. It is also possible that due to the higher hydrophobicity of these analogs when compared to HMBA, there is enhanced distribution of these compounds in the cells leading to improved biological activity (FIG. 2).

Some compounds were further evaluated at a lower concentration of 100 µM (FIG. 3). The compounds did not precipitate in cell culture, suggesting they were water soluble at 100 µM. Compounds 3c2, 2d1, 3d1, 2f2, 3f2, and 4a4 were not able to induce HEXIM1 expression, at 100 µM. However, compounds 3a2 and 3d2 showed significant activity at 100 µM that was not observed at 500 µM. The variation in potency could be due to the precipitation of the two compounds at 500 µM, which hampers cell penetration. Compounds 3b1 and 3b2 with the aromatic ring at B moiety showed good activity at 100 µM, and induced HEXIM1 expression by 3.8 and 2 fold, respectively. Compounds 2a4 and 2a5 exhibited reduced activity at lower concentrations, suggesting dose dependent stimulation of HEXIM1 expression by these compounds. Compound 4a1 showed similar activities at 100 and 500 µM. Due to the unsymmetrical structural characteristic of 4a, a dose-dependent study was performed and the results are presented in FIG. 4. The compound dose-dependently induced HEXIM1 expression suggesting that the unsymmetrical structure and increased hydrophobicity contribute to improved biological activity. Considering the aromatic moiety of compounds 3b1 and 3b2 and the bulky terminal moiety of compounds 2a4 and 2a5, more potent analogs could be developed if several of these structural units are combined in the new drug design.

In brief, this Example provides unique molecular scaffolds that significantly induced HEXIM1 expression in cancer cells. More potent HEXIM1 inducers have potential application in cancer, AIDS, and heart disease treatment.

Example 2

This Example shows the ability of HMBA derivative, 4a1 to induce known HMBA- and HEXIM1-induced activities, including regulation of the expression of HEXIM1 targets.

Methods

Cell Culture and Transfections

MCF7, MDA-MB-231, and LNCaP cells were obtained from the American Tissue Culture Collection, and were maintained as previously described. Construction of expression vectors for control miRNA or HEXIM1 miRNAs were described previously. MCF7 or LNCaP cells were transfected with expression vectors containing either the HEXIM1 miRNA insert or a control miRNA insert as previously described. Following blasticidin selection, cells expressing the highest level of GFP were flow-sorted and expanded. MDA-MB-231 cells were transfected with control or expression vector for Flag-tagged HEXIM1 as previously described. The tamoxifen resistant cells line (TOTR) was generated by serial passage of parental MCF7 cells in growth media supplemented with 1 uM trans-hydroxytamoxifen.

Western Blot

Cell lysates were analyzed by western blot as previously described. Anti-HEXIM1 was generated in the Montano laboratory. Primary antibodies against p21 (C-19; cat #sc-397), cyclin D1 (HD11; cat #sc-246) and myc (9E10; cat #sc-40) were obtained from Santa Cruz Biotechnology. Anti-GAPDH was obtained from Millipore. Anti-HIF-1α was obtained from Oxy-cell, Bioresearch).

Chromatin Immunoprecipitation

ChIP assays were carried out as previously described. Anti-CDK9 antibody (D-7; cat #sc-13130) was obtained from Santa Cruz Biotechnology.

Lipid Droplets (Nile Red Staining)

Cells were stained with Nile red for lipid droplets (marker of cell differentiation). Briefly, the stock solution of Nile red 1 mg/ml in acetone was diluted in PBS (1:1000). The fixed cells (4% paraformaldehyde) were incubated with diluted Nile red for 5 minutes at room temperature, rinsed with PBS and observed for the presence of lipid droplets by confocal microscopy. Images were digitally captured using a Leica microscope (Leica Microsystems Inc, IL, USA).

Proliferation Assay

MCF7 cells were plated onto 96 well plates and treated with 17β-estradiol±trans-hydroxytamoxifen in the presence of DMSO (vehicle), HMBA or 4a1 for 7 days. Cell proliferation was assessed using the MTT based Cell Growth Determination Kit from Sigma-Aldrich according to the manufacturer's protocol.

Results

Lead Optimization of HMBA to Develop Potent HEXIM1 Inducers

Our findings provide unique molecular scaffolds that significantly induced HEXIM1 expression in prostate cancer cells, and have opened a new lead optimization direction for HMBA. We observed increased potency of one of these compounds, 4a1 (FIG. 5A), when compared to HMBA in breast cancer MCF7 and MDA-MB-231 cells (FIGS. 5B and 5C), as we have previously observed in prostate cancer cells.

Induction of HEXIM1 Expression by HMBA and 4a1 Through Induction of CDK9 Recruitment to HEXIM1 Gene The induction of HEXIM1 by HMBA appears to involve the release of free P-TEFb from 7SK snRNP, and recruitment of P-TEFb to HEXIM1 gene. P-TEFb is a heterodimer between the cyclin-dependent kinase 9 (Cdk9) and its regulatory subunit Cyclin T1 (CycT1). We thus determined the regulation of the recruitment of CDK9 to the HEXIM1 coding sequence by HMBA and 4a1. Chromatin Immunoprecipitation (ChIP) assays indicate comparative ability of HMBA and 4a1 to induce recruitment of CDK9 to HEXIM1 gene in both MCF7 and LNCaP cells (FIG. 6).

HEXIM1 is Required for HMBA- and 4a1-Induced Cell Differentiation

HMBA was investigated in a Phase II clinical trial due to its potent anti-cancer and cell differentiation activities. Moreover, the roles of HMBA, and potentially 4a1, as differentiating factors are advantageous for their therapeutic use when compared to cytotoxic agents. We examined the relative role of HEXIM1 in HMBA-induced differentiation and regulation of expression of p21, which is known to promote cellular differentiation. We also examined the ability of 4a1 to induce differentiation and the relative role of HEXIM1.

HMBA and 4a1 induced p21 expression, and downregulation of HEXIM1 using HEXIM1 siRNA resulted in inhibition of HMBA- and 4a1-induced p21 expression in breast cancer MCF7 cells (FIG. 7A). We also observed induction of p21 expression by both HMBA and 4a1 in prostate cancer LNCaP cells (FIG. 7B). As we observed in breast cancer cells, induction was attenuated upon downregulation of HEXIM1 expression using shRNA in LNCaP cells. We also stained cells with Nile red to detect lipid droplets as a marker of differentiation. Both HMBA and 4a1 induced differentiation of MCF7 cells, and HEXIM1 is required for the induction of cell differentiation (FIG. 8A). Expression of Flag-tagged-HEXIM1 or treatment with HMBA or 4a1 induced differentiation of the triple negative MDA-MB-231 breast cancer cells (FIG. 8B). Together our findings in MCF7, MDA-MB-231, and LNCaP cells support a critical role of HEXIM1 as a mediator of HMBA and 4a1 actions.

HMBA and 4a1 Enhanced Sensitivity of Tamoxifen Resistant Breast Cancer Cells to Tamoxifen We have reported that HEXIM1 is required for the ability of antiestrogens to inhibit the activity of the Estrogen Receptor, that loss of HEXIM1 results in agonistic activity of tamoxifen, and that recurrence after tamoxifen therapy can be correlated with loss of HEXIM1 expression in human breast tissue samples. Thus we determined if HMBA and 4a1 can enhance sensitivity to tamoxifen of a tamoxifen resistant breast cancer line (MCF7/TOTR). This cell line was developed using long-term exposure to tamoxifen, which resulted in decreased sensitivity to inhibitory effects of tamoxifen (FIG. 9B). HEXIM1 protein expression is decreased in MCF7/TOTR when compared to parental MCF7 9 cells (FIG. 9A). However treatment with either HMBA or 4a1 induced HEXIM1 expression and enhanced the sensitivity of TOTR cells to trans-hydroxytamoxifen (FIG. 9B).

Regulation of the Expression of HEXIM1 Targets by HMBA and 4a1

To assess the clinical potential of HMBA and 4a1 we need to determine to what extent the targets of HMBA and 4a1 overlap with that of HEXIM1. We focused on direct targets of HEXIM1 that we have identified. 4a and HMBA regulated expression of proteins (FIG. 10) we have previously determined to be directly regulated by HEXIM1, and play critical roles in mammary tumorigenesis, angiogenesis, and metastasis.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of treating cancer in a subject in need thereof, the method comprising administering to cancer cells of the subject a therapeutically effective amount of a compound having the formula:

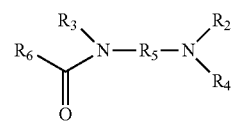

wherein $R_2$ is selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido, imino, alkylimino, arylimino, nitro (—NO$_2$), nitroso (—NO), sulfo (—SO$_2$—OH), sulfonato (—SO$_2$—O$^-$), $C_1$-$C_{24}$ alkylsulfanyl, arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide, phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, and phosphate esters;

R₃ and R₄ are the same or different and selected from the group consisting of hydrogen and substituted or unsubstituted $C_1$-$C_6$ alkyl;

R₅ is selected from the group consisting of a substituted or unsubstituted $C_2$-$C_6$ alkylene, $C_2$-$C_{24}$ alkenylene, $C_2$-$C_{24}$ alkynylene, $C_3$-$C_{20}$ arylene, heterocycloalkenylene containing from 5-6 ring atoms, heteroarylene or heterocyclylene containing from 5-14 ring atoms, $C_6$-$C_{24}$ alkarylene, and $C_6$-$C_{24}$ aralkylene;

wherein R₆ is selected from the group consisting of substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl ((CO)—NH₂), $C_1$-$C_{24}$ alkyl-carbamoyl (—(CO)—NH($C_1$-$C_{24}$ alkyl)), and arylcarbamoyl (CO)—NH-aryl);

R₆ is not a methyl group if R₅ is 1,6-hexylene, R₂ is an acetyl group, and R₃ and R₄ are hydrogen; and pharmaceutically acceptable salts thereof.

2. The method of claim 1, wherein the therapeutically effective amount is an amount effective to induce HEXIM1 expression in the cancer cells of the subject.

3. The method of claim 1, wherein the therapeutically effective amount is an amount effective to induce differentiation of the cancer cells.

4. The method of claim 1, wherein the cancer cells are metastatic cancer cells and the compound is administered to the metastatic cancer cells at an amount effective to inhibit at least one of cancer cell invasion, angiogenesis, and/or pre-metastatic niche formation.

5. The method of claim 1, wherein the compound exhibits negligible inhibition of histone diacetylene (HDAC) activity.

6. The method of claim 1, wherein the compound is administered to the subject as a pharmaceutical composition that includes the compound and the pharmaceutically acceptable carrier and the pharmaceutical composition administered to the subject induces HEXIM1 expression in the cancer cells without promoting thrombocytopenia in the subject.

7. The method of claim 1, wherein R₂ is selected from the group consisting of substituted or unsubstituted alkanesulfonyl, alkanesulfinyl, alkanoyl, benzoyl, and aroyl.

8. The method of claim 1, wherein R₅ is selected from the group consisting of propylene, butylene, pentylene, hexylene, heptylene, octylene, nonylene, dodecylene, cyclohexylene, 1,4-cylohexylene-bis(methylene), 1,4-cylohexylene-bis(ethylene), 1,4-cylohexylene-bis(propylene), phenylene, 1,4-phenylene-bis(methylene), 1,4-phenylene-bis(ethylene), and 1,4-phenylene-bis(propylene).

9. The method of claim 1, wherein the compound has the formula:

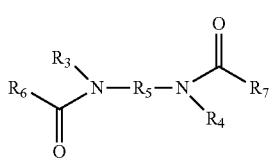

wherein R₆ and R₇ are the same or different and are selected from the group consisting of substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH₂), $C_1$-$C_{24}$ alkyl-carbamoyl (—(CO)—NH($C_1$-$C_{24}$ alkyl)),and arylcarbamoyl (—(CO)—NH-aryl);

at least one of R₆ or R₇ is not a methyl group if R₅ is 1,6-hexylene and R₃ and R₄ are hydrogen; and pharmaceutically acceptable salts thereof.

10. The method of claim 1, wherein the compound has the formula:

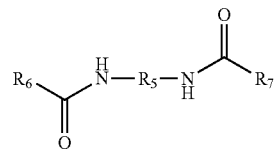

wherein R₆ and R₇ are the same or different and are selected from the group consisting of substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy (—O-acyl), $C_2$-$C_{24}$ alkoxycarbonyl (—(CO)—O-alkyl), $C_5$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH₂), $C_1$-$C_{24}$ alkyl-carbamoyl (—(CO)—NH($C_1$-$C_{24}$ alkyl)),and arylcarbamoyl (—(CO)—NH-aryl);

at least one of R₆ or R₇ is not a methyl group if R₅ is 1,6-hexylene; and pharmaceutically acceptable salts thereof.

11. The method of claim 9, wherein R₆ and R₇ are the same.

12. The method of claim 9, wherein R₆ and R₇ are different.

13. The method of claim 10, wherein R₆ is a substituted or unsubstituted $C_1$-$C_{24}$ alkyl and R₇ is selected from the group consisting of substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH₂), $C_1$-$C_{24}$ alkyl-carbamoyl (—(CO)—NH($C_1$-$C_{24}$ alkyl)),and arylcarbamoyl (—(CO)—NH-aryl).

14. The method of claim 1, wherein the compound has the formula:

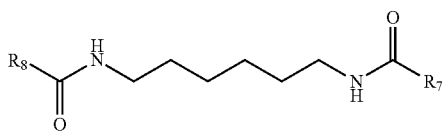

$R_7$ is selected from the group consisting of substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, and (—O-acyl);

$R_6$ is a linear or branched $C_1$-$C_{12}$ alkyl group; and pharmaceutically acceptable salts thereof.

15. The method of claim 1, further comprising administering an anti-cancer agent in combination with the compound, wherein the anti-cancer agent does not induce HEXIM1 expression in the cancer cell.

16. The method of claim 15, wherein the anti-cancer agent comprises at least one of radiation therapy or ionizing radiation, thermal stress or thermal therapy, irreversible electroporation (IRE), oxidative stress, and anti-proliferative agents.

17. The method of claim 1, wherein the compound is administered systemically to the subject.

18. The method of claim 1, wherein the compounds is administered directly to the cancer cells.

19. The method of claim 1, wherein the cancer comprises at least one of breast cancer, prostate cancer, neuroblastoma, glioblastoma, leukemia, lymphoma, myeloma, melanoma, or colon cancer.

20. The method of claim 1, wherein the cancer is metastatic breast cancer or metastatic prostate cancer and the compound is administered to the subject at an amount effective to inhibit metastasis of the cancer.

21. The method of claim 1, wherein the cancer is metastatic breast cancer and the method further comprises administering an estrogen receptor antagonist in combination with the compound.

* * * * *